United States Patent
Endress et al.

(10) Patent No.: US 8,603,746 B2
(45) Date of Patent: *Dec. 10, 2013

(54) METHODS FOR THE CYTOLOGICAL ANALYSIS OF CERVICAL CELLS

(75) Inventors: Gregory Anton Endress, Belchertown, MA (US); Madhvi Upender, Potomac, MD (US); Elizabeth Light, Gaithersburg, MD (US); Colyn Cain, Bethesda, MD (US)

(73) Assignee: NeoDiagnostix, Inc., Rockville, MD (US)

( * ) Notice: Subject to any disclaimer, the term of this patent is extended or adjusted under 35 U.S.C. 154(b) by 494 days.

This patent is subject to a terminal disclaimer.

(21) Appl. No.: 12/506,985

(22) Filed: Jul. 21, 2009

(65) Prior Publication Data

US 2010/0209913 A1    Aug. 19, 2010

Related U.S. Application Data

(60) Provisional application No. 61/082,346, filed on Jul. 21, 2008.

(51) Int. Cl.
*C12Q 1/68* (2006.01)

(52) U.S. Cl.
USPC ........................................................ 435/6.11

(58) Field of Classification Search
None
See application file for complete search history.

(56) References Cited

U.S. PATENT DOCUMENTS 5,919,624 A * 7/1999 Ried et al. ................... 435/6.14
2005/0026190 A1   2/2005 Sokolova et al.

FOREIGN PATENT DOCUMENTS

WO     2006-089287 A2    8/2006

OTHER PUBLICATIONS

Mainardi, Orphanet Journal of Rare Dieases, 2006, vol. 1:33, pp. 1-9.*
Zhang et al., Genes, Chromosomes & Cancer, 2002, 34, pp. 269-275.*
Cuzick et al., Vaccine, 2006, 24S3, pp. 90-97.*
Santin et al., Virology, 2005, 331, pp. 269-291.*
Ellis et al., Journal of Clinical PAthology, 2005, 58, pp. 710-714.*
Heselmeyer-Haddad et al. American J of Pathology, 2005, 4, pp. 1229-1238.*
Rudlowski et al., Anatomic Pathology, 2003, 120, pp. 691-698.*
Brown and Wahl, Cancer, 1993, 72, pp. 2979-2985.*
Grobholz et al., Cancer Research, 1993, 53, pp. 4204-4211.*
Godoy et al., J of Cellular Physiology, 2006, 207, 614-27.*
Wilting et al., J. Pathol. 2006; 209: 220-230.
Fitzpatrick, MA et al., Gyenecology Oncol 2006, 103: 458-462.
Hopman, Ahn et al., J Pathol 2006, 210:412-419.
Heselmeyer-Haddad, K et al., Am J Pathol 2005, 166:1229-1238.
Huang, FY et al., Cancer Genet Cytogenet 2005, 157:42-48.
Heselmeyer-Haddad, K et al. Am J Pathol 2003, 163: 1406-1416.
Rao, PH et al., BMC Cancer 2004, 4:5-13.
Heselmeyer et al., Genes, Chromosomes & Cancer 1997:233-240.
Heselmeyer et al., PNAS 1996, 93:479-484.
Andersson et al., British Journal of Cancer 2006, 1-8.
Atkin, NB 1997 Elsevier, 95:33-39.
Arias-Pulido, H. et al., 2002 Mol. Cancer; 1:3.
Macville, M. et al., 1999 Cancer res; 59:141-50.
Lockwood, W. et al., Int. J. Cancer 2006; 120:436-443.
Takuma, Y. et al., 2004 Journal of Gastroenterology and Hepatology; 19:1300-1304.
Takahashi, S. et al., 2000 Eropean Journal of Cancer; 36:496-502.
Toshikuni, N. et al. 2000 Br. J. Cancer; 82:833-837.
Zhang, A. et al., 2000 Cancer Res.; 60:6230-6235.
Zhang, A. et al. 2002 Genes Chromosomes Cancer; 34:269-75.
Huang, K.F. et al., J. Formos Med Asoc Nov. 2007 106 (11):894-902.
Jee, K.J. et al., Mod Pathol. May 2001: 14(5):377-81.
Caraway, NP. et al, Gynecol. Oncol. Jul. 2008: 110(1):37-42. Epub Apr. 22, 2008.
Cao, Y. et al., Cancer Sci Jun. 2008: 99(6):1092-1099.
Wolf, D.J. et al. (2007) Period Guidelines for Fluorescence In Situ Hybridization Testing.
Anju Zhang et.al., Genetic Alterations in Cervical Carcinomas: Frequent Low-Level Amplifications of Oncogenes are Associated with Human Papilloma Virus Infection, Int. J. Cancer 101, 427-433 (2002).
Online Mendelian Inheritance in Man® (OMIM®), entry No. 123450, "Cri-du-Chat Syndrome", Creation date Apr. 14, 1994.

* cited by examiner

*Primary Examiner* — Anne Gussow
*Assistant Examiner* — Mindy G Brown
(74) *Attorney, Agent, or Firm* — Michele M. Wales; InHouse Patent Counsel, LLC

(57) ABSTRACT

The invention provides for a diagnostic test to monitor cancer-specific genetic abnormalities to diagnose cervical cell disorders and predict which patients might progress to cancer. Genetic abnormalities are detected by identification in chromosomal copy number of chromosome 3 and chromosome 5 using FISH analysis of probes targeted to 3q and/or 5p.

100 Claims, 17 Drawing Sheets

A

B

A

B

C

| GENE NAME | CHROMOSOME LOCATION | RefSeq NUMBER |
|---|---|---|
| PPM1L | 3q26.1 | NM_139245 |
| B3GALNT1 | 3q26.1 | NM_003781 |
| NMD3 | 3q26.1 | NM_015938 |
| C3orf57 | 3q26.1 | NM_001040100 |
| OTOL1 | 3q26.1 | NM_001080440 |
| SI | 3q26.1 | NM_001041 |
| SLITRK3 | 3q26.1 | NM_014926 |
| BCHE | 3q26.1 | NM_000055 |
| ZBBX | 3q26.1 | NM_024687 |
| WDR49 | 3q26.1 | NM_178824 |
| SERPINI2 | 3q26.1 | NM_006217 |
| PDCD10 | 3q26.1 | NM_145859 |
| SERPINI1 | 3q26.1 | NM_001122752 |
| GOLIM4 | 3q26.2 | NM_014498 |
| C3orf50 | 3q26.2 | NR_021485 |
| EVI1 | 3q26.2 | NM_001105077 |
| MDS1 | 3q26.2 | NM_004991 |
| TERC | 3q26.2 | NR_001566 |
| ARPM1 | 3q26.2 | NM_032487 |
| MYNN | 3q26.2 | NM_018657 |
| LRRC34 | 3q26.2 | NM_153353 |
| LRRIQ4 | 3q26.2 | NM_001080460 |
| LRRC31 | 3q26.2 | NM_024727 |
| SAMD7 | 3q26.2 | NM_182610 |
| LOC100128164 | 3q26.2 | NR_027622 |
| LOC100128164 | 3q26.2 | NR_024409 |
| SEC62 | 3q26.2 | MN_003262 |
| GPR160 | 3q26.2 | NM_014373 |
| PHC3 | 3q26.2 | NM_024947 |
| PRKCI | 3q26.2 | NM_002740 |
| SKIL | 3q26.2 | NM_005414 |

FIG. 14A

| GENE NAME | CHROMOSOME LOCATION | RefSeq NUMBER |
|---|---|---|
| CLDN11 | 3q26.2 | NM_005602 |
| SLC7A14 | 3q26.2 | NM_020949 |
| RPL22L1 | 3q26.2 | NM_001099645 |
| EIF5A2 | 3q26.2 | NM_020390 |
| SLC2A2 | 3q26.2 | NM_000340 |
| TNIK | 3q26.2 | NM_001161560 |
| PLD1 | 3q26.31 | NM_002662 |
| FNDC3B | 3q26.31 | NM_022763 |
| GHSR | 3q26.31 | NM_198407 |
| TNFSF10 | 3q26.31 | NM_003810 |
| AADACL1 | 3q26.31 | NM_001146276 |
| ECT2 | 3q26.31 | NM_018098 |
| SPATA16 | 3q26.31 | NM_031955 |
| NLGN1 | 3q26.31 | NM_014932 |
| NAALADL2 | 3q26.31 | NM_207015 |
| TBL1XR1 | 3q26.32 | NM_024665 |
| KCNMB2 | 3q26.32 | NM_181361 |
| ZMAT3 | 3q26.32 | NM_152240 |
| PIK3CA | 3q26.32 | NM_006218 |
| KCNMB3 | 3q26.32 | NM_171830 |
| ZNF639 | 3q26.33 | NM_016331 |
| MFN1 | 3q26.33 | NM_033540 |
| GNB4 | 3q26.33 | NM_021629 |
| ACTL6A | 3q26.33 | NM_004301 |
| MRPL47 | 3q26.33 | NM_020409 |
| NDUFB5 | 3q26.33 | NM_002492 |
| USP13 | 3q26.33 | NM_003940 |
| PEX5L | 3q26.33 | NM_016559 |
| TTC14 | 3q26.33 | NM_001042601 |
| CCDC39 | 3q26.33 | NM_181426 |
| FXR1 | 3q26.33 | NM_001013438 |
| DNAJC19 | 3q26.33 | NM_145261 |
| SOX2OT | 3q26.33 | NR_004053 |
| SOX2 | 3q26.33 | NM_003106 |
| ATP11B | 3q26.33 | NM_014616 |
| DCUN1D1 | 3q26.33 | NM_020640 |

FIG. 14B

| GENE NAME | CHROMOSOME LOCATION | RefSeq NUMBER |
|---|---|---|
| PLEKHG4B | 5p15.33 | NM_052909 |
| LOC389257 | 5p15.33 | NM_001080478 |
| CCDC127 | 5p15.33 | NM_145265 |
| SDHA | 5p15.33 | NM_004168 |
| PDCD6 | 5p15.33 | NM_013232 |
| AHRR | 5p15.33 | NM_020731 |
| C5orf55 | 5p15.33 | NM_138464 |
| EXOC3 | 5p15.33 | NM_007277 |
| LOC25845 | 5p15.33 | NR_024158 |
| SLC9A3 | 5p15.33 | NM_004174 |
| CEP72 | 5p15.33 | NM_018140 |
| TPPP | 5p15.33 | NM_007030 |
| ZDHHC11 | 5p15.33 | NM_024786 |
| BRD9 | 5p15.33 | NM_001009877 |
| TRIP13 | 5p15.33 | NM_004237 |
| NKD2 | 5p15.33 | NM_033120 |
| SLC12A7 | 5p15.33 | NM_006598 |
| SLC6A18 | 5p15.33 | NM_182632 |
| SLC6A19 | 5p15.33 | NM_001003841 |
| TERT | 5p15.33 | NM_198255 |
| CLPTM1L | 5p15.33 | NM_030782 |
| SLC6A3 | 5p15.33 | NM_001044 |
| LPCAT1 | 5p15.33 | NM_024830 |
| SDHAP3 | 5p15.33 | NR_003263 |
| LOC728613 | 5p15.33 | NR_003713 |
| MRPL36 | 5p15.33 | NM_032479 |
| NDUFS6 | 5p15.33 | NM_004553 |
| IRX4 | 5p15.33 | NM_016358 |
| IRX2 | 5p15.33 | NM_001134222 |
| C5orf38 | 5p15.33 | NM_178569 |
| IRX1 | 5p15.33 | NM_024337 |
| LOC340094 | 5p15.32 | NR_026994 |
| ADAMTS16 | 5p15.32 | NM_139056 |
| KIAA0947 | 5p15.32 | NM_015325 |
| FLJ33360 | 5p15.31 | NM_001001702 |
| MED10 | 5p15.31 | NM_032286 |

FIG. 14C

| GENE NAME | CHROMOSOME LOCATION | RefSeq NUMBER |
|---|---|---|
| FLJ25076 | 5p15.31 | NM_001145161 |
| LOC255167 | 5p15.31 | NR_024424 |
| NSUN2 | 5p15.31 | NM_017755 |
| SRD5A1 | 5p15.31 | NM_001047 |
| POLS | 5p15.31 | NM_006999 |
| ADCY2 | 5p15.31 | NM_020546 |
| C5orf49 | 5p15.31 | NM_001089584 |
| FASTKD3 | 5p15.31 | NM_024091 |
| MTRR | 5p15.31 | NM_002454 |
| SEMA5A | 5p15.31 | NM_003966 |
| SNORD123 | 5p15.31 | NR_003689 |
| TAS2R1 | 5p15.31 | NM_019599 |
| LOC285692 | 5p15.31 - 5p15.2 | NR_027112 |
| FAM173B | 5p15.2 | NM_199133 |
| CCT5 | 5p15.2 | NM_012073 |
| CMBL | 5p15.2 | NM_138809 |
| MARCH6 | 5p15.2 | NM_005885 |
| ROPN1L | 5p15.2 | NM_031916 |
| DAP | 5p15.2 | NM_004394 |
| CTNND2 | 5p15.2 | NM_001332 |
| DNAH5 | 5p15.2 | NM_001369 |
| TRIO | 5p15.2 | NM_007118 |
| FAM105A | 5p15.2 | NM_019018 |
| FAM105B | 5p15.2 | NM_138348 |
| ANKH | 5p15.2 | NM_054027 |
| FBXL7 | 5p15.1 | NM_012304 |
| MARCH11 | 5p15.1 | NM_001102562 |
| ZNF622 | 5p15.1 | NM_033414 |
| FAM134B | 5p15.1 | NM_001034850 |
| MYO10 | 5p15.1 | NM_012334 |
| LOC285696 | 5p15.1 | NR_027253 |
| BASP1 | 5p15.1 | NM_006317 |

FIG. 14D

METHODS FOR THE CYTOLOGICAL ANALYSIS OF CERVICAL CELLS

FIELD

The invention relates to methods and kits for the analysis of chromosomal abnormalities in cervical cells.

BACKGROUND

Cervical cancer is one of the most common and deadly cancers among women worldwide. If detected early, cervical cancer and precursor lesions can be treated effectively. A Pap test is the primary screen for cervical cancer and uses morphological analysis to identify suspicious cells. However, a single cytologic examination is relatively insensitive, poorly reproducible and frequently yields equivocal results. Approximately 6% of Papanicolaou (Pap) tests are diagnosed as atypical squamous cells of undetermined significance (ASCUS) and require follow-up testing, and 5-10% of ASCUS patients have undetected cancer. Current guidelines for patients include follow-up Pap testing, testing for human papilloma virus (HPV) and/or colposcopy.

Infection with HPV is associated with cervical cancer and many patients are tested for HPV after an ASCUS Pap test result. The strength of sensitive HPV testing is that it provides extremely high negative predictive value; women who test negative are at low risk for developing cervical cancer. However, the positive predictive value of HPV testing is limited since only a small fraction of HPV positive early lesions progress to high-grade dysplasia and cancer. Thus, HPV detection, even in combination with cytomorphological evaluation, is a test with poor specificity.

In addition, approximately 3% of Pap tests are diagnosed with low-grade squamous intraepithelial lesions (LSIL). Current guidelines for these patients recommend additional monitoring and/or colposcopy. Clinical studies show the majority of these patients are HPV+.

There is significant risk for an ASCUS/HPV+ or LSIL patient to progress to more severe cervical disease and require surgical treatment in the two years following the initial test. The identification of these patients that will progress is impossible based on morphology and HPV infection. Genetic alterations have been identified in the early development of cervical cancer that can predict the patient's risk of disease progression. These aberrations include gross changes in DNA content (e.g. ploidy) and the amplification of both a portion of chromosome 3, specifically locus 3q26, that includes a gene TERC that encodes a subunit the telomerase protein and a portion of chromosome 5, specifically 5p15, that includes a gene, TERT, that encodes another subunit of the telomerase protein, both of which are linked to cell immortality. Studies have demonstrated multicolor fluorescent DNA probes can detect abnormalities in both ploidy, and 3q and 5p copy number by fluorescence in situ hybridization (FISH) with greater sensitivity and specificity than other methods.

The implementation of cervical cancer screening programs has greatly reduced disease incidence and mortality in industrialized countries. However, a single cytological evaluation remains relatively insensitive, hence the need for frequent follow-up investigations. This is attributable to sampling or interpretation errors, and to the fact that some early lesions may not have acquired recognizable phenotypic alterations. Invasive cervical carcinomas develop through increasing stages of cervical dysplasia, to cervical intraepithelial neoplasia (CIN) 1, CIN2, CIN3 and to carcinoma in situ, which is considered a bonafide precancerous lesion that requires surgical intervention. However, only about 15% of all low-grade dysplastic lesions follow this path of linear progression. Pap and HPV tests are indirect methods for determining the presence of cervical dysplasia or cancer. Therefore, there is a continuing unmet need for the methods of using molecular markers for directly identifying the presence of dysplasia or cancer and monitoring disease progression.

SUMMARY

The invention provides for a diagnostic method to monitor genetic changes in cervical cells using various cytological methods for detecting hybridization using FISH, CISH, flow cytometry, or other methods as are known to those of skill in the art and for detecting genetic abnormalities to predict which patients might progress to cancer and those unlikely to progress, months, if not years, before traditional symptoms present.

The visualization of chromosomal aneuploidy and copy number changes of specific cancer-associated genes has become an important complement to routine morphological assessment of cytological samples. This approach is biologically valid and successful because chromosomal aneuploidy and the resulting genomic imbalances are specific for cancer cells, distinct for different carcinomas, and occur early during disease progression. Like most other human carcinomas, cervical cancers are defined by a distribution of genomic imbalances. In addition to infection with high-risk subtypes of human papilloma virus, the sequential transformation of cervical squamous epithelium requires the acquisition of additional copies of chromosome arm 3q and 5p, among other cytogenetic abnormalities. In an aspect of the invention, identification of a 3q26 amplification in addition to amplification of 5p15 in low grade cervical dysplasia can provide information regarding the progressive potential of individual lesions to high grade cervical dysplasia and cancer.

In one aspect, the present invention provides a method for assessing a patient condition of cervical cell disorder which may include cervical dysplasia or cancer comprising: detecting, in a sample from a patient: a genomic amplification in chromosome 3q; a genomic amplification in chromosome 5p; and the presence and/or amplification of the centromere of chromosome 7 (CEN7) as control. Detecting the genomic amplification of chromosome 3q and chromosome 5p indicates progression of the patient condition to high grade cervical dysplasia. Detection of genomic amplification of chromosome 7 measures the general ploidy status of the cervical cell. Typically copy number changes in chromosome 7 do not occur during early stage cervical carcinogenesis. If genomic amplification of chromosome 7 is present, it indicates aneuploidy, a state associated with advanced pre-cancers and cancers. The method can assess a change of patient condition of low grade cervical dysplasia to a condition of high grade cervical dysplasia or cancer.

In yet another aspect of the invention, a method for monitoring a shift from a low grade to a condition of high grade cervical dysplasia in a patient is provided for. In certain aspects of the invention, the methods disclosed comprise assessing a change in a patient condition of low grade cervical dysplasia to a condition of high grade cervical dysplasia; identifying a patient at risk of developing invasive cervical carcinoma; and assessing maintenance of a patient condition of low grade cervical dysplasia or regression of a patient condition to low grade cervical dysplasia or normal.

In a specific aspect, the methods disclosed herein can further comprise, in addition to detecting genetic amplification in chromosome 3q and 5p, detecting amplification in chromosomes: 1q; 20q; 12q; 19q; 11q; 6q; 17p; 7; 8q (detected in late stage dysplasia); 9q; 16q; 2q; 9p; 10q; 18p and any combination thereof. According to more specific aspects of the invention, amplification in the 3q26 locus and 5p15 locus is detected. In addition to detection of the 3q26 and 5p15 loci, amplification in the following chromosomal loci can be detected: 1q21-31; 20q12; 12q13-24; 19q13; 11q21; 7q11-22; 8q24 (detected in late stage dysplasia); 9q33;-34; 16q23; 2q32; 9p22; 10q21-24; 18p11 and any combination thereof.

The methods disclosed herein can further comprise determining that the genomic amplification of chromosome 3q and/or chromosome 5p is present in the sample or that the genomic amplification of chromosome 3q and/or chromosome 5p is not present in the sample.

In another aspect of the inventions, probes directed to chromosomal regions disclosed are provided, and kits are provided for conducting methods of the invention.

These and other aspects of some exemplary embodiments will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments without departing from the spirit thereof.

DESCRIPTION OF THE DRAWINGS

FIG. 8A is from a CIN1 tissue biopsy. FIG. 8B is from a CIN2 biopsy.

FIG. 9A is from a CIN1 tissue biopsy. FIG. 9B is from a CIN2 tissue biopsy. FIG. 9C is from a CIN3 tissue biopsy.

FIGS. 14 A, B, C, and D illustrate a listing of genes that can be targeted by specific probes of the invention to measure chromosomal abnormalities in cervical cells.

DETAILED DESCRIPTION

Figure 1:
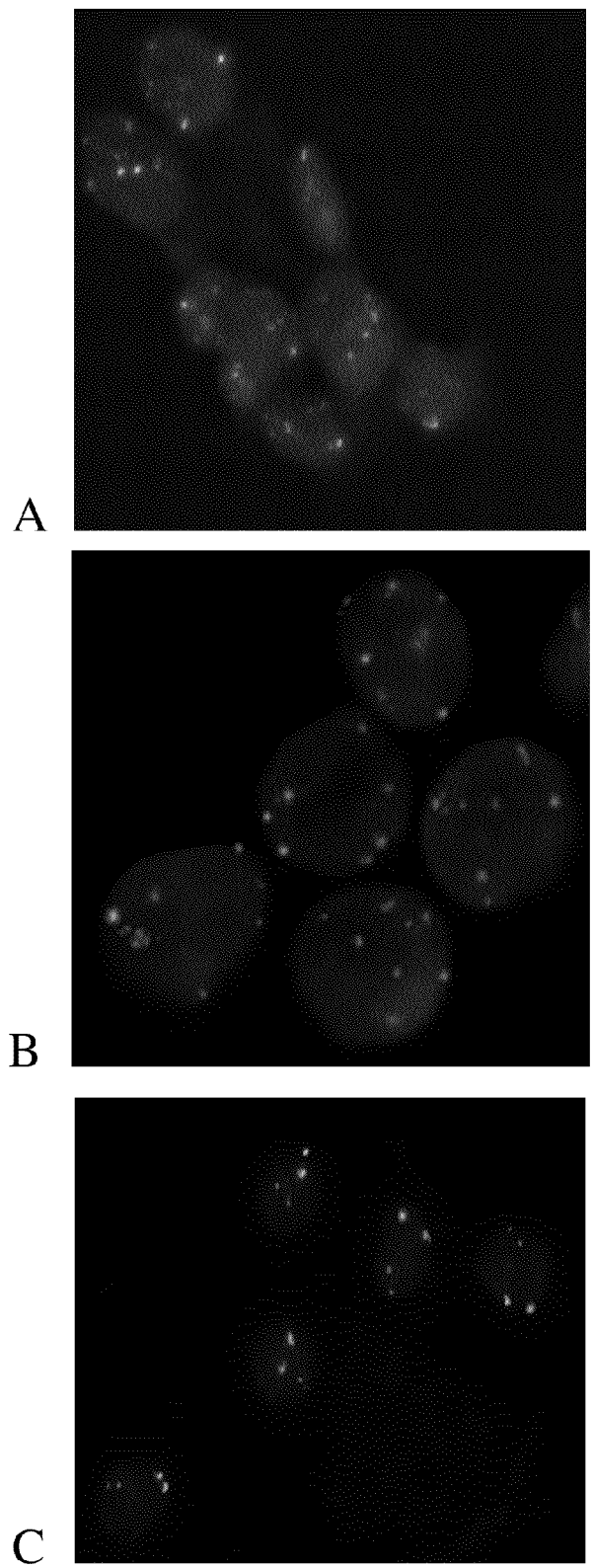
FIGS. 1A, B and C illustrate the stages of cervical cancer progression as represented by amplification of 3q26 chromosomal copy number gain.
Figure 2:
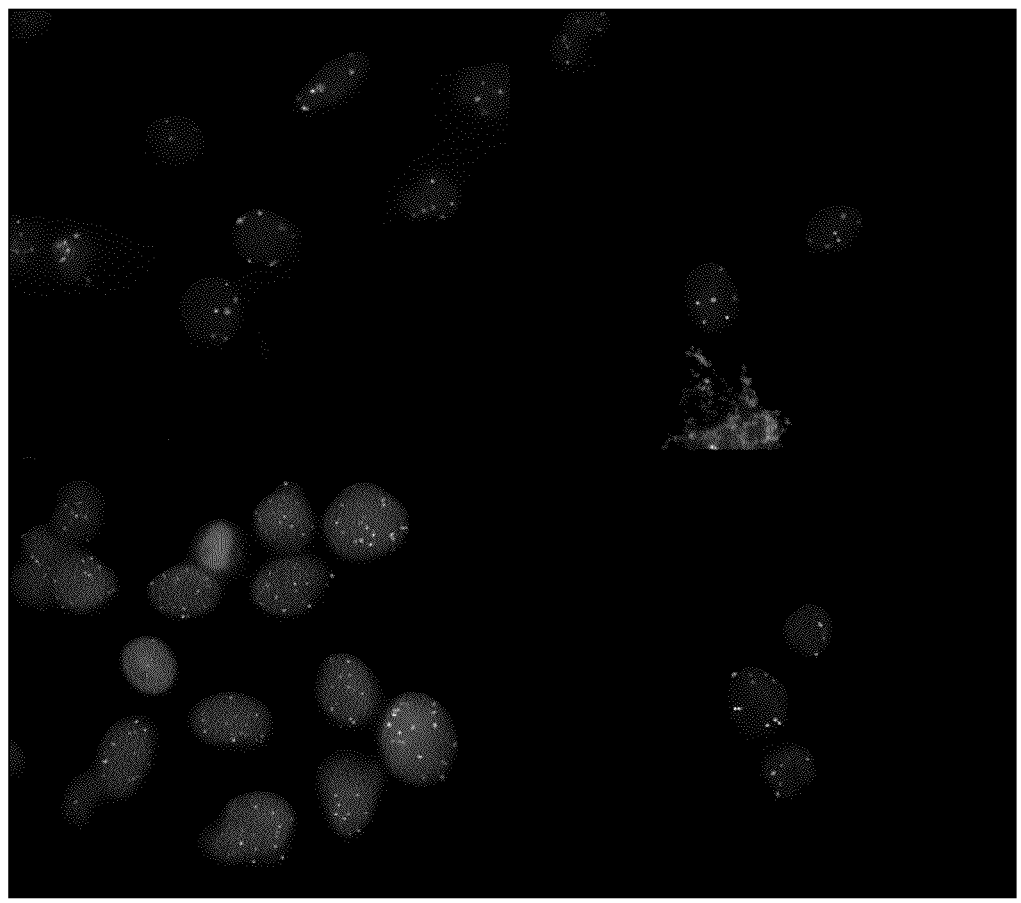
FIG. 2 illustrates the stages of cervical cancer progression as represented by amplification of 3q26 and 5p15 chromosomal copy number gain.
Figure 3:
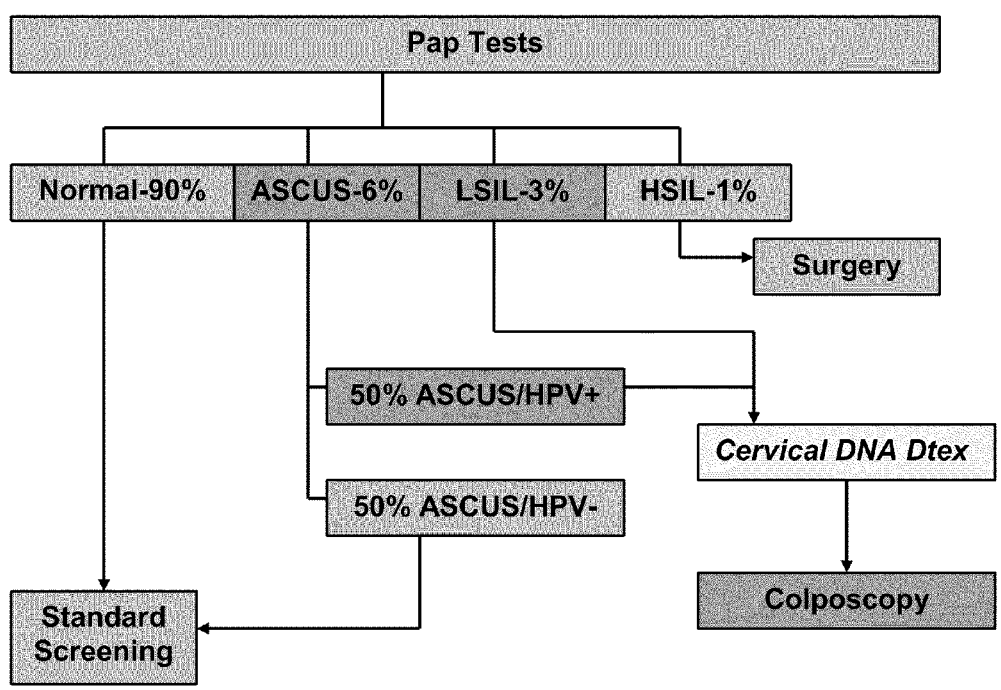
FIG. 3 illustrates the patient management process for cervical cancer detection following Pap tests.

The present invention is based on the identification of gain in copy number of chromosomal regions associated with cervical cancer. Cancer is a genetic disease, and genetic aberrations can be observed in diseased cells. The aberrations can be observed cytologically, by measuring genetic aberrations either as increase or decrease in gene regions. Also, certain gene expression differences are evident in cancer cells such that measurement of biomarker expression can be a diagnostic indicator of disease state in the cell, whether or not it can be observed cytologically. The methods discussed herein can directly identify abnormalities in the DNA of cervical cells using fluorescently labeled probes that bind to the aberrant regions in the chromosome. When greater than, or less than, the expected number of signals are observed, a cell sample can be diagnosed as diseased and cervical dysplasia can be diagnosed before it can be observed cytologically. Patients with these abnormalities can have a poor prognosis and can be at high risk to develop more advanced cervical disease. The methods disclosed herein can be performed subsequent to or in lieu of ASCUS/HPV+ or LSIL Pap tests, among other abnormal results from cytology testing, in order to provide more specific information about a patient's risk of disease progression.

As used herein, "cervical cell disorder," "cervical disorder," or "cervical disease" means any of the following: cervical carcinogenesis, Negative for Intraepithelial Lesion or Malignancy (NILM), Human Papilloma Virus (HPV) positive, Atypical Squamous Cells of Undetermined Significance (ASC-US), Low-grade Squamous Intraepithelial Lesion (LSIL), Atypical Squamous Cells, HSIL (ASC-H), Atypical Glandular Cells of Undetermined Significance (AGUS), High-grade Squamous Intraepithelial Lesion (HSIL), cervical dysplasia, pre-cancer, pre-malignant legion, cervical cancer, cervical adenocarcinoma, cervical squamous cell carcinoma, cervical intraepithelial neoplasia 1 (CIN1), cervical intraepithelial neoplasia (CIN2), cervical intraepithelial neoplasia 3 (CIN3), carcinoma in situ, invasive cervical carcinoma, and cytological or genetic abnormality of the cell. Also, "disease," "cell disorder," or "disorder" as used herein includes but is not limited to any cytological or genetic abnormality of the cell.

The present method provides direct identification of genetic abnormalities in morphologically normal cells and abnormal cells, as well as prognostic information about disease progression, and the flexibility to work with both squamous and glandular cervical cells.

Copy Number Gains

An increase in 3q copy number, in addition to integration of human papilloma virus (HPV) into the host genome, have been associated with the progression of CIN2 or CIN 3 to cervical carcinoma such that both appear to be important associated events in the progression of cervical dysplasia to invasive cancer. Hopman et al. J. Pathol. 2006 December: 210(4): 412-9. Higher staged tumors or those with lymph node metastasis had more chromosomal imbalances including gains of 3q; 1q; 8q; and losses of 11q; 3q; 6q and 2q. Gains of 3q11-q22 and 3q26-qter were more prevalent with lymph node metastasis. Huang, K. F. et al., J. Formos Med Assoc. 2007 November; 106(11): 894-902.

3q gains seen in invasive cervical carcinomas, specifically gain in the human telomerase gene (TERC), have been used in the development of FISH probe sets as a diagnostic tool in the detection of TERC gains in Pap smears. It has been suggested that TERC gains could predict progression from CIN1/CIN2 to CIN3 and invasive carcinoma. Heselmeyer-Haddad et al. Am Journal of Pathology 2005; 166:1229-1238.

5p is also a frequently observed structurally changed chromosome in carcinomas. Atkin, N. B 1997 Elsevier; 95: 33-39. Arias-Pulido, H. et al. 2002 Mol. Cancer; 1:3. Huang F. Y., et al. 2005 Cancer Gen. and Cyto., 157: 46-47. Macville M., et al. 1999 Cancer Res.; 59:141-50. Heselmeyer K. et al. 1997 Genes Chromosomes Cancer; 19: 233-40. Rao P. H. et al. 2004 BMC Cancer; 4:5. 5p gains are observed during progression to advanced stage carcinomas, and frequently involve whole arm amplifications. Heselmeyer K. et al. 1997 Genes Chromosomes Cancer; 19: 233-40.

Using carcinoma cell lines that showed 5p amplification, a minimal region of alteration at 5p13.33 has been defined, which encodes the human telomerase reverse transcriptase (hTERT) gene. Lockwood, W. et al. Int. J. Cancer 2006; 120: 436-443. Finally, an HPV integration site has also been mapped to 5p11-15. Lockwood, W. et al. Int. J. Cancer 2006; 120: 436-443. Telomerase activation is a component of cancer cell immortality Takuma, Y. et al. 2004 Journal of Gastroenterology and Hepatology; 19: 1300-1304. Takahashi S. et al. 2000 Eur. Jour. Of Cancer, 36: 496-502. Toshikuni, N. et al. 2000 Br. J. Cancer; 82; 833-837. hTERT has been identified as the catalytic subunit of telomerase. Takahashi S. et al. 2000 Eur. Jour. Of Cancer, 36: 496-502.

hTERT expression has been observed in several cancer cell lines, including cervical carcinomas, with certain cancer cell lines showing that hTERT expression is high in cancerous lesions but not non-cancerous tissues. Takahashi S. et al. 2000 Eur. Jour. Of Cancer, 36: 496-502. Although this differential expression was found in hepatocarcinomas rather than cervical carcinomas, the results suggest that hTERT expression occurred at an early stage of hepatocarcinogenesis. Takahashi S. et al. 2000 Eur. Jour. Of Cancer, 36: 496-502. Further, 5p hTERT gene amplification is closely correlated with increased hTERT mRNA expression in cervical cancers with HPV infection. Zhang A. et al. 2000 Cancer Res.; 60: 6230-6235. Zhang A. et al. 2002 Genes Chromosomes Cancer; 34: 269-75. 5p has been consistently identified as a chromosome that undergoes structural changes during various stages of carcinogenesis. The structural changes also appear to consistently affect the TERT gene encoded on 5p.

5p gain has been observed in invasive cervical carcinoma. Scotto, et al., Molecular Cancer 2008. When observed in samples in addition to observations of gain in 3q, specifically 3q26, it can be an indicator of increased progression of disease state from cervical dysplasia to invasive cervical carcinoma. Using a genomic probe for a region on 3q, specifically chromosome band 3q26, in combination with at least one control probe, (eg. CEP3, CEN7), and a genomic probe for a region on 5p, especially 5p15, the copy number increases precede malignant conversion of cervical intraepithelial neoplasms to invasive carcinoma, and further accompany the transition from ASCUS or CIN1 to CIN2 or CIN3 and from CIN2 or CIN3 to carcinoma in situ to invasive cervical carcinoma. Moreover, the identification of gain in both 3q and 5p indicates an expedited transition from ASCUS or CIN1 to CIN2 or CIN3 and from CIN2 or CIN3 to carcinoma in situ to invasive cervical carcinoma.

The present methods provide for identification of possible cervical cell disorder by comparing the copy number increase of the target chromosomes, for example, 5p, 3q or both together, as compared to normal. As used herein, "normal" means chromosomal diploidy in mammalian cells except when cells that are normally diploid are tetraphase and in the cell cycle and tetraploidy is observed.

All cells have a normal complement of 23 pairs of chromosomes a state that is described as diploid. However, when cells grow and undergo cell division they generate a second set of 23 pairs of chromosomes one set will subsequently reside in the two daughter cells that are created. This state is described as tetraploid. While tetraploidy is a natural process that occurs throughout the body's tissues and organs on a regular basis, it occurs at low frequency, in general. One hallmark of cancer is uncontrollable cell growth and replication. This typically occurs due to multiple abnormalities in the chromosomes of the cell that enable the cell to escape the standard replication control systems within normal cells. These multiple abnormalities within the chromosomes lead to a state described as aneuploidy, where the chromosome complement is no longer 23 pairs, but something else. Typically, aneuploid cells have extra copies of some chromosomes, have lost other chromosomes, and have even created hybrid chromosomes by fusing two or more together. Very active cell division and tetraploidy provides a foundation for aneuploid cells to develop. Tetraploid can, therefore, be a transitory condition that indicates a higher risk level for the development of aneuploid cells and more severe cell disorders. Therefore, these methods can measure tetraploidy and provide for the identification of cervical cell disorder and possible progression to cervical cancer according to the methods disclosed herein.

Methods

The methods can be used as a diagnostic and prognostic marker for cervical dysplasia. Patients with ploidy abnormalities and/or increased 3q and/or increased 5p copy numbers have a poor prognosis and are at high risk to develop more advanced cervical disease.

It is an embodiment of the present invention to identify changes in DNA content and 3q+5p copy number in cervical cytology samples using multicolor FISH probes directed to loci on chromosomes 5p and 3q and directed to CEN7, more specifically, the probes are directed to 5p15 and 3q26. In a preferred embodiment, probes to different targets will fluoresce with a different color so that targets can be differentiated.

It is an embodiment of the present invention to provide a method for assessing a patient condition of cervical dysplasia or cancer, comprising, detecting in a sample from a patient: a genomic amplification in chromosome 3q; a genomic amplification in chromosome 5p; the presence and/or amplification of CEN7. Detecting the genomic amplification of chromosome 3q and chromosome 5p indicates progression of the patient condition from low grade to high grade cervical dysplasia.

The methods of the invention can be used to monitor a shift from a low grade to a condition of high grade cervical dysplasia in a patient sample: a genomic amplification in chromosome 3q; a genomic amplification in chromosome 5p; the presence and/or amplification of CEN7. Detecting the genomic amplification of chromosome 3q and chromosome 5p indicates progression of the patient condition to high grade cervical dysplasia.

The methods disclosed herein may further comprise, in addition to detecting genetic amplification in chromosome 3q and 5p, detecting amplification in chromosomes: 1q; 20q; 12q; 19q; 11q; 6q; 17p; 7; 8q (detected in late stage dysplasia); 9q; 16q; 2q; 9p; 10q; 18p and any combination thereof.

According to specific embodiments of the invention, amplification in the 3q26 locus and 5p15 locus band, including the Cri du Chat region, can be detected. In yet further specific embodiments of the invention, in addition to detection the 3q26 and 5p15 loci, amplification in the following chromosomal loci can be detected: 1q21-31; 20q12; 12q13-24; 19q13; 11q21; 7q11-22; 8q24 (detected in late stage dysplasia); 9q33-34; 16q23; 2q32; 9p22; 10q21-24; 18p11 and any combination thereof.

The method can further comprise determining that the genomic amplification of chromosome 3q and/or chromosome 5p is not present in the sample. When compared to a state where aneuploidy is found and cervical cell disorder is identified, the loss of chromosomal amplification can be indicative of regression of cell disorder and possibly regression of disease.

The methods may be used for assessing and monitoring late stage dysplasia comprising detecting genomic amplification in chromosomes 3q, as well as 5p and 8q, more specifically 8q24. Gain of 8q copy number and/or gain in 5p copy number in combination with gain in 3q, can indicate malignant conversion of cervical intraepithelial neoplasms to invasive carcinoma, and further accompany the transition from ASCUS/CIN1 to CIN2/CIN3 and from CIN2/CIN3 to carcinoma in situ to invasive cervical carcinoma. Moreover, the identification of gain in both 3q and 5p indicates an expedited transition from ASCUS/CIN1 to CIN2/CIN3 and from CIN2/CIN3 to carcinoma in situ to invasive cervical carcinoma.

The methods further provide for a specific probe panels including probes to chromosomes 3q and 5p, and can further include probes to: 1q; 20q; 12q; 19q; 11q; 6q; 17p; 7; 8q (detected in late stage dysplasia); 9q; 16q; 2q; 9p; 10q; 18p and any combination of probes thereof. According to specific embodiments of the aforementioned probe panel, probes to the 3q26 locus and 5p15 locus, including the Cri du Chat region, in addition to, probes to the following chromosomal loci can be used: 1q21-31; 20q12; 12q13-24; 19q13; 11q21; 7q11-22; 8q24 (detected in late stage dysplasia); 9q33;-34; 16q23; 2q32; 9p22; 10q21-24; 18p11 and any combination thereof.

One of skill in the art can prepare nucleic acid probes that are complimentary to the sequences of the loci described herein. Additionally, many such probes are commercially available.

Recent clinical research has illuminated the role of HPV infections is the development of anal cancers. In fact, the Centers for Medicare and Medicaid Services (CMS) recently began providing coverage for a range of cytology and HPV testing of anal specimens. Because of the similar biology between cervical and anal carcinogenesis, including similar cell types and viral initiation, genomic abnormalities and copy number changes occur at 3q and 5p among other loci. It is therefore a further embodiment of the present invention to analyze anal cell specimens for 3q and 5p among the other chromosomal copy number changes to determine whether a patient may have anal disease. Therefore, these methods could be used on anal specimens and provide valuable clinical information regarding anal carcinogenesis.

Probes

A number of methods can be used to identify probes which hybridize specifically to the specific loci exemplified herein. For instance, probes can be generated by the random selection of clones from a chromosome specific library, and then mapped by digital imaging microscopy. This procedure is described in U.S. Pat. No. 5,472,842. Various libraries spanning entire chromosomes are also available commercially from for instance Illumina Inc. Probes that hybridize specific chromosomal loci are available commercially from Abbot Molecular, Inc. (Des Plaines., Ill.)

Briefly, a genomic or chromosome specific DNA is digested with restriction enzymes or mechanically sheared to give DNA sequences of at least about 20 kb and more preferably about 40 kb to 300 kb. Techniques of partial sequence digestion are well known in the art. See, for example Perbal, A Practical Guide to Molecular Cloning, 2nd Ed., Wiley N.Y. (1998). The resulting sequences are ligated with a vector and introduced into the appropriate host. Exemplary vectors suitable for this purpose include cosmids, yeast artificial chromosomes (YACs), bacterial artificial chromosomes (BACs) and P1 phage. Various libraries spanning entire chromosomes are also available commercially from for instance Genome Systems.

Once a probe library is constructed, a subset of the probes is physically mapped on the selected chromosome. FISH and digital image analysis can be used to localize clones along the desired chromosome. Briefly, the clones are mapped by FISH to metaphase spreads from normal cells using e.g., FITC as the fluorophore. The chromosomes may be counterstained by a stain which stains DNA irrespective of base composition (e.g., DAPI or propidium iodide), to define the outlining of the chromosome. The stained metaphases are imaged in a fluorescence microscope with a polychromatic beam-splitter to avoid color-dependant image shifts. The different color images are acquired with a CCD camera and the digitized images are stored in a computer. A computer program is then used to calculate the chromosome axis, project the two (for single copy sequences) FITC signals perpendicularly onto this axis, and calculate the average fractional length from a defined position, typically the p-telomere. This approach is described, for instance, in U.S. Pat. No. 5,472,842.

Sequence information of the genes identified here permits the design of highly specific hybridization probes or amplification primers suitable for detection of target sequences from these genes. As noted above, the complete sequence of these genes is known. Means for detecting specific DNA sequences within genes are well known to those of skill in the art. For instance, oligonucleotide probes chosen to be complementary to a selected subsequence within the gene can be used. Alternatively, sequences or subsequences may be amplified by a variety of DNA amplification techniques (for example via polymerase chain reaction, ligase chain reaction, transcription amplification, etc.) prior to detection using a probe. Amplification of DNA increases sensitivity of the assay by providing more copies of possible target subsequences. In addition, by using labeled primers in the amplification process, the DNA sequences may be labeled as they are amplified.

In one embodiment, probes of the present invention may be directed to at least a portion of TERC gene at band 3q26.2 and TERT or TRIP13 at 5p15.3. Specifically, a probe to TERC at region 3q26 of approximately 495 kb can be used labeled with spectrum gold and also a probe for 5p15 labeled with spectrum green. Such probes are commercially available from Abbot Molecular (Des Plaines, Ill.). However, the probes of the invention can include any gene on the 3q26 and 5p15 including genes in the Cri du Chat region and those listed in FIGS. 16A-D and any combination or portion of the genes on 3q26 or 5p15.

In a specific embodiment, the detectable marker of the probe can emit a fluorescent signal or the probe may be chromogenic. The probes are hybridized using fluorescent in situ hybridization (FISH). FISH is a cytogenetic technique used to detect or localize the presence or absence of specific DNA sequences on chromosomes. FISH uses fluorescent probes that bind to parts of the chromosome with which they show a high degree of sequence similarity. Fluorescence microscopy can be used to find out where the fluorescent probe binds to the chromosome. In situ hybridization is a technique that allows the visualization of specific nucleic acid sequences within a cellular preparation. Specifically, FISH involves the precise annealing of a single stranded fluorescently labeled DNA probe to complementary target sequences. The hybridization of the probe with the cellular DNA site is visible by direct detection using fluorescence microscopy.

In instances where additional genetic material is required for testing, the genome may be amplified or detected by Polymerase Chain Reaction (PCR).

It is yet another embodiment of the invention to provide for a procedure of performing FISH on liquid cytology specimens such as SUREPATH® or THINPREP® specimens for successful hybridization of DNA probes in practicing the methods disclosed herein. SUREPATH® is available from Becton-Dickinson of Sparks, Md. THINPREP® is available from Hologic Laboratories of Bedford, Mass.

It is yet another aspect of the invention to use antibodies to separate squamous and glandular cells out of liquid-based cytology specimens prior to detecting genetic amplification in sample cells. The separation of cell types can improve detection of both squamous and glandular cancers and improve detection of cervical carcinomas which are rarely detected through traditional Pap testing but show 3q26 amplification, 5p15 amplification, or both.

The present methods can utilize probes that are fluorescently labeled nucleic acid probes for use in in situ hybridization assays. The labeled probe panel may consist at least of a three-color, three-probe mixture of DNA probe sequences homologous to specific regions on chromosomes 3, 5 and 7; and, as well as other chromosome regions disclosed herein.

As used herein "label" or "labels" is any composition, e.g. probe, detectable by spectroscopic, photochemical, biochemical, immunochemical, or chemical means including but not limited to fluorescent dyes (e.g. fluorescein, rhodamine, Texas Red, etc., enzymes, electron dense reagents, magnetic labels, and the like). Labels which are not directly detected but are detected through the use of indirect label include biotin and dioxigenin as well as haptens and proteins for which labeled antisera or monoclonal antibodies are available. Methods of labeling nucleic acids and probes are well known to those of skill in the art. Preferred labels are those that are suitable for use in in situ hybridization. The nucleic acid probes may be detectably labeled prior to hybridization. Alternatively, a detectable label which binds to the hybridization product may be used. Such detectable labels include any material having a detectable physical or chemical property and are well developed in the field of immunoassays.

It is yet another embodiment of the present methods whereby squamous and/or glandular cervical cells can be used from a patient sample to assess chromosomal abnormalities using the present methods.

Typically, it is desirable to use multiple color, in a preferred embodiment three-color FISH methods for detecting chromosomal abnormalities in which three probes are utilized, each labeled by a different fluorescent dye. In the preferred embodiment, two test probes that hybridizes to the regions of interest are labeled with two different dyes and a control probe that hybridizes to a different region is labeled with a third dye. More than three probes can be used so long as each is labeled with a unique dye. A nucleic acid probe that hybridizes to a stable region of the chromosome of interest such as the centromere, is preferred as a control probe so that differences between efficiency of hybridization from sample to sample can be determined.

Cells recovered and isolated from specimens or samples collected from patients can be fixed on slides. Specimens can be retrieved using various techniques known in the art. In one embodiment specimens can be retrieved from THINPREP® and/or SUREPATH® samples. SUREPATH® is a Pap test used for the screening of cervical cancer. SUREPATH® has various collection devices to collect Pap samples from a patient. Some have detachable heads that hold the sample, are directly detached and put into a vial that is sent for screening, enabling 100% of sample to be available for processing. A liquid-based Pap test using thin-layer cell preparation process called the BD SUREPATH® liquid-based Pap test which claims an increase in detection rate compared to the conventional Pap smear is used with the SUREPATH® collection devices such as the broom-like device or the brush/spatula with detachable heads, as disclosed in U.S. patent application Ser. No. 11/521,144, incorporated herein by reference in its entirety. The THINPREP® Pap is a liquid-based cytology method. A sample of the cervical cells is rinsed into a vial instead of a smear onto a slide thus preventing clumping of cells. The cells are separated in a laboratory to eliminate blood and mucus and the cells to be studied are then placed on a slide for studies to detect cancerous cells.

The samples may also comprise analysis of tissue from cervical biopsies, punch biopsies, surgical procedures including LEEP, hysterectomy, CONE biopsy, ECC. The sample may be prepared from tissue or cells removed from the cervix, vagina or vulva.

Hybridization

In an embodiment, the regions disclosed here are identified using in situ hybridization. Generally, in situ hybridization comprises the following major steps: (1) fixation of tissue or biological structure to be analyzed; (2) pre-hybridization treatment of the biological structure to increase accessibility of target DNA, and to reduce nonspecific binding; (3) hybridization of the mixture of nucleic acids to the nucleic acid of the biological sample or tissue; (4) post-hybridization washes to remove nucleic acid fragments not bound in the hybridization and (5) detection of the hybridized nucleic acids. Hybridization protocols for the applications described herein are described in U.S. Pat. No. 6,277,563, incorporated herein by reference in its entirety.

From samples, the target DNA can be denatured to its single stranded form and subsequently allowed to hybridize with the probes of the method. Following hybridization, the unbound probe is removed by a series of washes, and the nuclei are counterstained with DAPI (4,6 diamidino-2-phenylindole), a DNA-specific stain. Hybridization of the DNA probes can be viewed using a fluorescence microscope equipped with appropriate excitation and emission filters allowing visualization of the aqua and gold fluorescent signals. Enumeration of CEN 7, 5p15 and 3q26 signals is conducted by microscopic examination of the nuclei.

The clinical test disclosed herein can use several biomarkers in combination for the early detection of cervical cancer and is important because current morphology based screening and detection methods have significant limitations. Identification of 3q26 and 5p15, among others, amplification and other cytogenetic abnormalities can more precisely and accurately identify patients at risk for developing cervical cancer and help them receive earlier treatment.

Image Analysis

It is an embodiment of the present invention to provide for automatic image analysis and scoring of the methods disclosed. In situ hybridization is a technique that allows the visualization of specific nucleic acid sequences within a cellular preparation. Specifically, DNA fluorescence in situ hybridization (FISH) involves the precise annealing of a single stranded fluorescently labeled DNA probe to complementary target sequences. The hybridization of the probe with the cellular DNA site is visible by direct detection using fluorescence microscopy. The method, as described herein, utilizes probes that are fluorescently labeled nucleic acid probes for use as part of in situ hybridization assays. In a preferred embodiment, the probe panel consists of a 3-color, three-probe mixture of DNA probe sequences homologous to specific regions on chromosomes 3, 5, and 7. The probe mixture consists of a locus specific probe for chromosome 3q26, 5p15, and centromere of chromosome 7 (CEN7).

It is an embodiment of the present invention to provide for automated image analysis of the signal from the FISH probe. Microscopes can allow for automated capture of digital images of the field of view within the specimen/slide on the microscopy stage. Such manufacturers include Carl Zeiss, Leica, Nikon and Olympus. Also, the method provides for software platforms for automated image analysis such as microscope-software systems developed by such entities as Ikonisys of Connecticut, Metasystems of Massachusetts and Germany and Bioimagene of California, Bioview of Massachusetts, and Israel, among others. Such automated systems may apply to viewing 3q chromosomes alone or in combination with 5p abnormalities in the patient sample.

Cells recovered from specimens can be fixed on slides. The target DNA is denatured to its single stranded form and subsequently allowed to hybridize with the probes. Following hybridization, the unbound probe can be removed by a series of washes, and the nuclei are counterstained with DAPI (4,6 diamidino-2-phenylindole), a DNA-specific stain. Hybridization of the probes can be viewed using a fluorescence microscope equipped with appropriate excitation and emission filters allowing visualization of the three fluorescent signals. Enumeration of CEN7, 5p15 and 3q26 signals is conducted by automated microscopic examination of the nuclei.

The probe set and DAPI counterstain can be viewed on an epi-fluorescence microscope equipped with a 100-watt mercury lamp equipped with the following filters: DAPI, Spectrum Aqua (chromosome 7 centromere), Spectrum Green (locus on 5p15), and Spectrum Orange (locus on 3q26) or other labels and probes as are known in the art and disclosed herein. DAPI filter and a magnification of 100× can quickly scan sample area of patient slide to determine cell quantity and quality. Analysis begins in the upper left quadrant of the target area. Scan fields with 63× oil objective from left to right and top to bottom, without re-scanning the same areas. The system can count a total of 1000 cells. The method further comprises automatic scoring of the cell counts.

Clinical Significance of Slide Analysis Procedure: While the performance of FISH laboratory procedures on specimens can be challenging, the resulting procedural analysis needs to be placed within context of the disease and the relevance of the technical results to clinical practice must be determined. The method disclosed herein is designed to be a direct evaluation of chromosomal copy number at specific loci associated with cervical cell disorders. The presence of these genetic abnormalities in cervical cancer screening specimens, such as a Pap test, long before the development of cancer has implications for the management and treatment of patients. The results of a FISH-based analysis of the specimen can be considered within clinical care guidelines and procedures.

Determination of chromosomal copy number in at least 800 cells, and preferably 1000 cells, can be a sufficient sampling of each clinical specimen. Less than 800 cells or more than 1000 cells can be utilized in this system. The method and system overcome sampling variations and limitations of slide production methodology. The methods and system are consistent with methods recommended by professional medical organizations (ACMG) to determine the threshold between a specimen with and without chromosomal copy number changes. Wolf, D. J. et al. (2007) Period Guidelines for Fluorescence In Situ Hybridization Testing.

The automated method and system provides for at least 90% accuracy for positive specimens and identifies a patient with an increased risk of disease progression. The method and system can further provide for greater than 95% accuracy.

In situ hybridization is a technique that allows the visualization of specific nucleic acid sequences within a cellular preparation. Traditionally the visualization of probe signals has been performed manually by highly-trained personnel. However, it is possible to adapt current technology to automate the image acquisition and analysis process. Microscopes on the market today, such as those manufactured by Carl Zeiss, Leica, Nikon, and Olympus, allow the user to capture digital images of the field of view within the specimen/slide on the microscopy stage. Some of these manufacturers have software available for the automated acquisition of images from specimens/slide. In addition, several entities (Ikonisys, Metasystems, Bioimagene, BioView, Aperio, Ventana, among others) have created software platforms specifically for use in commercial laboratories. Some of these entities have systems that include both a microscopy platform and the automated imaging software, including the Ikoniscope Digital Microscopy System by Ikonisys and Metafer and Metacyte by Metasystems.

The type and source of the specimen to be analyzed directly impacts the analysis process and methodology. Each tissue type has its own biology and structure plus each cancer develops differently with different factors affecting the rate of carcinogenesis. Therefore the present invention provides for several methods for automated image acquisition and analysis of specimens.

It is an embodiment of the system and method to be used in conjunction with specimens in liquid suspension that can be placed onto a microscope slide in an even, monolayer of cells, this includes liquid-base cytology specimens such as THINPREP® and SUREPATH® plus any fine-needle aspirate (FNA), sputum, or swab-based collection. This automated method screens the entire area covered by cells on the FISH prepared slide and utilizes the DAPI-stain to identify cellular nuclei. The system then enumerates each probe signal within the DAPI-stained region and records the copy number of each probe identified. The software system continues its automated scoring of cells and chromosomal copy number within each cell until it obtains results of at least 800 cells. Once the 800 cell threshold is reached, the software can categorize each cell imaged and counted into a category based upon the copy number of each chromosome identified. A normal cell with two copies of each probe 3q26, 5p15, and CEN7 would be placed into a 2,2,2 category. Abnormal cells would be identified by their probe signal patterns. For instance, a cell with two copies of the CEN7 probe, 5 copies of the 3q26 probe and 3 copies of the 5p15 probe can be placed in the 2,5,3 category. Once all of the imaged cells are categorized, the specimen can be evaluated relative to the positive/negative disease threshold. All cells identified as abnormal by the automated imaging system can be reviewed and verified manually by trained personnel before test results are communicated to a physician. The method and system further provides for automated verification. Specific cell threshold numbers can vary by specimen type and collection method. In addition, the software can be adapted to reflect biological (cell shape, cell size, DNA content of the nucleus, proximity of cells to each other, cell type, etc.) or disease related differences (number of loci with abnormal number, the number of abnormalities at a locus within a single cell, relationship of an abnormality to survival or treatment response). This method and system can be used on a representative sampling of area covered by cells on the slide instead of the entire area, typically this is performed by imaging multiple fields of view or a path based on cellular density until the minimum imaged cell threshold is met.

It is yet a further embodiment of the system and method that it can also be used in conjunction with specimens in liquid suspension that can placed onto a microscope slide in an even, monolayer of cells, this includes liquid-base cytology specimens such as THINPREP® and SUREPATH® plus any fine-needle aspirate (FNA), sputum, or swab-based collection. This automated method screens the entire area covered by cells on the FISH prepared slide and utilizes the DAPI-stain to identify cellular nuclei. The system then enumerates each probe signal within the DAPI-stained region and records the copy number of each probe identified. The software system continues its automated scoring of cells and chromosomal copy number within each cell until it obtains results of all of the cells on the slide. Once all of the cells are imaged, the software categorizes each cell imaged and counted into a category based upon the copy number of each chromosome identified. For instance, a normal cell with two copies of each probe 3q26, 5p15, and CEN7 would be placed into a 2,2,2 category. Abnormal cells would be identified by their probe signal patterns. For instance, a cell with two copies of the CEN7 probe, 5 copies of the 3q26 probe and 3 copies of the 5p15 probe would be placed in the 2,5,3 category. Once all of the cells are imaged, counted and categorized, the software identifies the cells with the greatest number of abnormalities and provides a descending rank-based ordering of the highly abnormal cells. This rank-based ordering of the highly abnormal cells within the specimen can be evaluated relative to the positive/negative disease threshold. Typically, but not always, cells identified as abnormal by the automated imaging system are reviewed and verified manually by trained personnel before test results are communicated electronically via methods known in the art to a physician. Specific cell threshold numbers can vary by specimen type and collection method. In addition, the software can be adapted to reflect biological (cell shape, cell size, DNA content of the nucleus, proximity of cells to each other, cell type, etc.) or disease related differences (number of loci with abnormal number, the number of abnormalities at a locus within a single cell, relationship of an abnormality to survival or treatment response). The present embodiments can be used on a representative sampling of area covered by cells on the slide instead of the entire area, typically this is performed by imaging multiple fields of view or a path based on cellular density until the minimum imaged cell threshold is met. Only a subset of the rank-ordered abnormal cells can be reviewed relative to the positive/negative test threshold as long as the clinical and disease significance is known for the subset. Typically the subset is the most abnormal 25 or 50 cells within the specimens, but other subsets can be identified and utilized depending on the specimen source, collection method, and disease.

Yet another embodiment can be used in conjunction with tissue-based specimens such as those from a biopsy or surgical procedure. In addition, this system and method can use a companion slide that is stained with hematoxylin and eosin stain (H&E) that comes from the same tissue-based specimen. This automated method screens the entire area covered by tissue-based specimen on the FISH prepared slide and utilizes the DAPI-stain to identify cellular nuclei. The system then enumerates each probe signal within the DAPI-stained region and records the copy number of each probe identified. The software system continues its automated scoring of cells and chromosomal copy number within each cell until the entire tissue-based specimen has been reviewed. The software then evaluates a sub-section of the slide that contains at least 25 nuclei as identified by the DAPI stain. The selection on the sub-section location is guided based upon disease indicators on the companion H&E slide. Typically, at least two sub-sections are selected for each specimen. The software then categorizes each cell imaged and counted into a category based upon the copy number of each chromosome identified. For instance, a normal cell with two copies of each probe 3q26, 5p15, and CEN7 would be placed into a 2,2,2 category. Abnormal cells would be identified by their probe signal patterns. For instance, a cell with two copies of the CEN7 probe, 5 copies of the 3q26 probe and 3 copies of the 5p15 probe would be placed in the 2,5,3 category. Once all of the imaged cells are categorized, the number of probe signals identified is compared to the total number of nuclei counted by the system to generate a ratio of chromosomal copy number per locus versus the number of cell counted. Once the ratio for each chromosomal loci is determined, the specimen can be evaluated relative to the positive/negative disease threshold. Typically, all sub-sections of the specimens identified with an abnormal ratio by the automated imaging system are reviewed and verified manually by trained personnel before test results are communicated to a physician. Specific sub-section size and number of nuclei counted can vary by specimen type and collection method. In addition, the software can be adapted to reflect biological (cell shape, cell size, DNA content of the nucleus, proximity of cells to each other, cell type, location within the tissue, amount of cytoplasm, etc.) or disease related differences (number of loci with abnormal number, the number of abnormalities at a locus within a single cell, relationship of an abnormality to survival or treatment response, location of the abnormalities within the tissue-based specimen, etc.).

In yet another embodiment, the system and method can be used in conjunction with tissue-based specimens such as those from a biopsy or surgical procedure. This automated method screens the entire area covered by tissue-based specimen on the FISH prepared slide and utilizes the DAPI-stain to identify cellular nuclei. The system then enumerates each probe signal within the DAPI-stained region and records the copy number of each probe identified. The software system continues its automated scoring of cells and chromosomal copy number within each cell until the entire tissue-based specimen has been reviewed. The software then evaluates a sub-section of the slides that contains at least 25 nuclei as identified by the DAPI stain. Typically, at least two sub-sections are selected for each specimen. The software then categorizes each cell imaged and counted into a category based upon the copy number of each chromosome identified. For instance, a normal cell with two copies of each probe 3q26, 5p15, and CEN7 would be placed into a 2,2,2 category. Abnormal cells would be identified by their probe signal patterns. For instance, a cell with two copies of the CEN7 probe, 5 copies of the 3q26 probe and 3 copies of the 5p15 probe would be placed in the 2,5,3 category. Once all of the imaged cells are categorized, the number of probe signals identified is compared to the total number of nuclei counted by the system to generate a ratio of chromosomal copy number per locus versus the number of cell counted. Once the ratio for each chromosomal loci is determined, the specimen can be evaluated relative to the positive/negative disease threshold. Typically, all sub-sections of the specimens identified with an abnormal ratio by the automated imaging system are reviewed and verified manually by trained personnel before test results are communicated to a physician. Specific sub-section size and number of nuclei counted can vary by specimen type and collection method. In addition, the software can be adapted to reflect biological (cell shape, cell size, DNA content of the nucleus, proximity of cells to each other, cell type, location within the tissue, amount of cytoplasm, etc.) or disease related differences (number of loci with abnormal number, the number of abnormalities at a locus within a single cell, relationship of an abnormality to survival or treatment response, location of the abnormalities within the tissue-based specimen, etc.).

The scoring data can be analyzed by calculating the number of any one of the signals (e.g. 3q, 5p, or CEN7) and dividing by the total number of nuclei scored; recording that number in the chart at the top of the Score Sheet. A result greater than 2 recorded and reported as amplified for any given probe.

The scoring data is analyzed by adding the number of any one of the signals (3q, 5p, or CEN 7) and dividing by the total number of nuclei scored. A result greater than 2 can be reported as amplified for the given probe. Images are named by the specimen number and slide number and saved.

In other embodiments, the present invention provides for kits for the detection of chromosomal abnormalities at the regions disclosed. In a preferred embodiment, the kits include one or more probes to the regions described herein and any combination of the disclosed probes. The kits can additionally include instruction materials describing how to use the kit contents in detecting the genetic alterations. The kits may also include one ore more of the following: various labels or labeling agents to facilitate the detection of the probes, reagents for the hybridization including buffers, an interphase spread, bovine serum albumin and other blocking agents including blocking probes, sampling devices including fine needles, swabs, aspirators and the like, positive and negative hybridization controls and other controls as are known in the art.

The following illustrative explanations of the figures and related examples are provided to facilitate understanding of certain terms used frequently herein, particularly in the examples. The explanations are provided as a convenience and are not limitative of the invention.

EXAMPLES

Example 1

FISH was performed on previously prepared thin layer, liquid-based cytology samples (THINPREP®, Cytyc, Marlborough, Mass.). Slides were made from THINPREP® vials and then subject to a pretreatment protocol that includes protease digestion, formaldehyde fixation, washing, and dehydration. Hybridization was performed using a two-color multi-target interphase FISH probe kit (Abbot Molecular). The kit included directly labeled probes to CEN7-aqua and to the locus of 3q26 (3q-orange) and to the locus of 5p15 (5p-green). The cells were analyzed using fluorescence microscopy.

Samples had a minimum of 800 cells for analysis. Positive tests showed aneuploidy and (1) gains of either 3q copy number or 5p copy number in 1.0% or more of the analyzed cells; (2) gains of only 3q copy number of 0.9% or more of the analyzed cells; or (3) gains of only 5p copy number in 0.7% or more of the analyzed cells. Negative tests showed normal ploidy and (1) less than 1.0% of analyzed cells with an increase in both 3q copy number and 5p copy number; (2) gains of only 3q copy number in less than 0.9% of the analyzed cells; or (3) gains of only 5p copy number in less than 0.7% of the analyzed cells. Samples with ploidy abnormalities and/or increased 3q copy number were determined to have a poor prognosis and risk to develop more advanced cervical disease.

Results can be a diagnostic and prognostic marker for cervical dysplasia. Samples with ploidy abnormalities and/or increased 3q copy number and 5p copy number were determined to have a poor prognosis and risk to develop more advanced cervical disease.

Example 2

Figure 6:
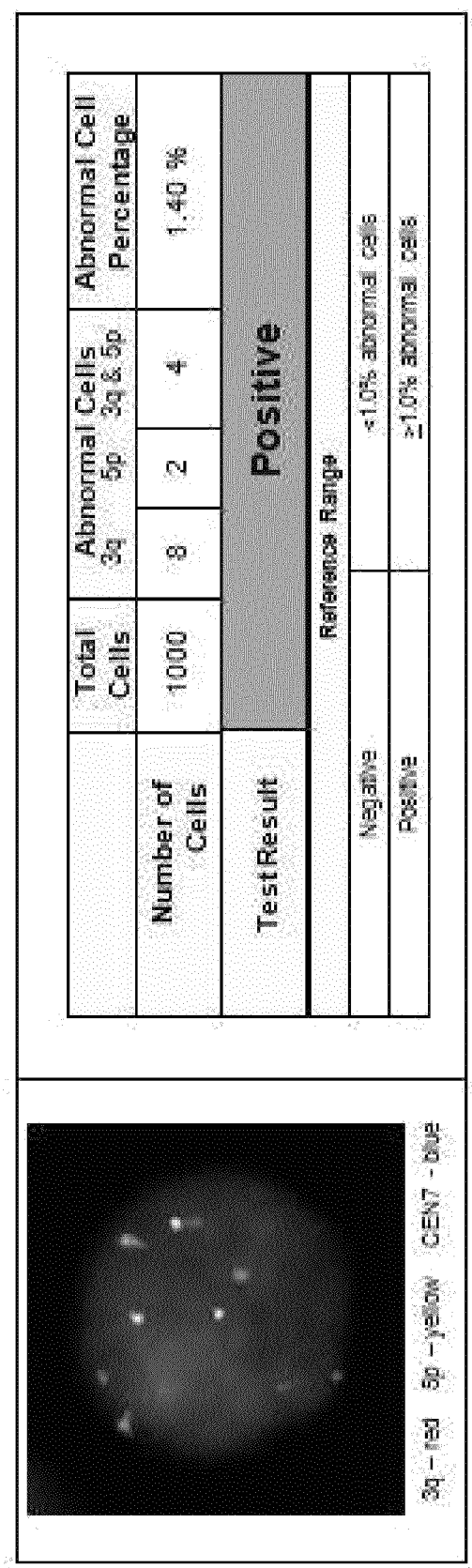
FIG. 6 is an illustration of positive results from a liquid-based cytology patient sample testing for abnormalities in 3q and 5p. Interpretation: Evaluation of this specimen has revealed an abnormal copy number of chromosomal regions 3q26 and 5p15. Gain of chromosomal region of 3q26 has been shown to be an early indicator of cervical dysplasia, while an increase in copy number at 5p15 is more often associated with advanced stages of cervical carcinoma. Detailed results of the analysis are summarized in the table above, along with a representative image of a cell(s) with an abnormal copy number of region 3q26 and/or 5p15. Materials and Methods: Analysis of gene specific loci at chromosomal regions 3q26 and 5p15 was performed using FISH with a probe specific for the TERC gene on chromosome region 3q26 and the Cri du Chat locus at 5p15. In addition, a probe specific for chromosome 7 centromere was applied to assess DNA ploidy. Cervical cells were fixed to a slide and hybridized with these fluorescent probes. Analysis of the hybridization was performed to assess the presence of normal and abnormal cells.

Evaluation of FIG. 6 this specimen has revealed an abnormal copy number of the TERC gene on 3q26 and the Cri du Chat locus 5p15. Of 1000 cells analyzed, 986 cells were normal while 8 were found abnormal for extra copies of TERC (3q), 2 were found abnormal for extra copies of Cri du Chat (5p), and 4 were found abnormal for extra copies of TERC and Cri du Chat (3q and 5p) for an abnormal cell percentage of 1.40%.

Example 3

Figure 7:
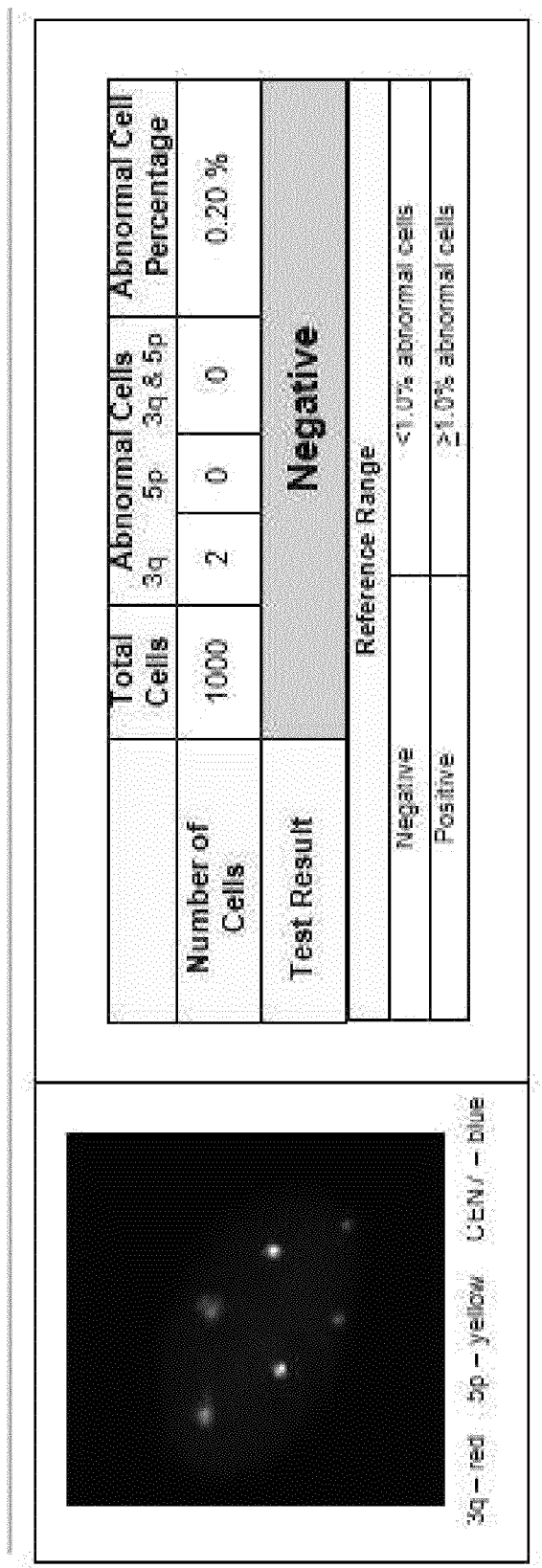
FIG. 7 is an illustration of negative results from a liquid-based cytology patient sample testing for abnormalities in 3q and 5p. Interpretation: Evaluation of this specimen has revealed a normal copy number of chromosomal regions 3q26 and 5p15. In the cells analyzed, amplification of loci at 3q26 and 5p15 was not detected and evaluation of the chromosome 7 centromere indicates a normal diploid specimen. Detailed results of the analysis are summarized in the table above, along with a representative image of a cell(s) with an abnormal copy number of region 3q26 and/or 5p15. Materials and Methods: Analysis of gene specific loci at chromosomal regions 3q26 and 5p15 was performed using FISH with a probe specific for the TERC gene on chromosome region 3q26 and the Cri du Chat locus at 5p15. In addition, a probe specific for chromosome 7 centromere was applied to assess DNA ploidy. Cervical cells were fixed to a slide and hybridized with these fluorescent probes. Analysis of the hybridization was performed to assess the presence of normal and abnormal cells.

Evaluation of FIG. 7 this specimen has revealed a normal copy number of the TERC gene on 3q26 and the Cri du Chat locus on 5p15. Of 1000 cells analyzed, 998 cells were normal while 2 were found abnormal for extra copies of TERC (3q), 0 were found abnormal for extra copies of Cri du Chat (5p), and 0 were found abnormal for extra copies of TERC and Cri du Chat (3q and 5p) for an abnormal cell percentage of 0.20%.

Example 4

Analysis for the Human Telomerase gene (TERC), 3q26, was performed using Fluorescent In-Situ Hybridization (FISH) with a probe specific for the TERC gene on chromosome region 3q26. In addition, a probe specific for CEN7 was applied to assess DNA ploidy. Cervical cells were fixed to a slide and hybridized with these fluorescent probes. Analysis of the hybridization was performed to assess the presence of normal and abnormal cells.

Example 5

Figure 5:
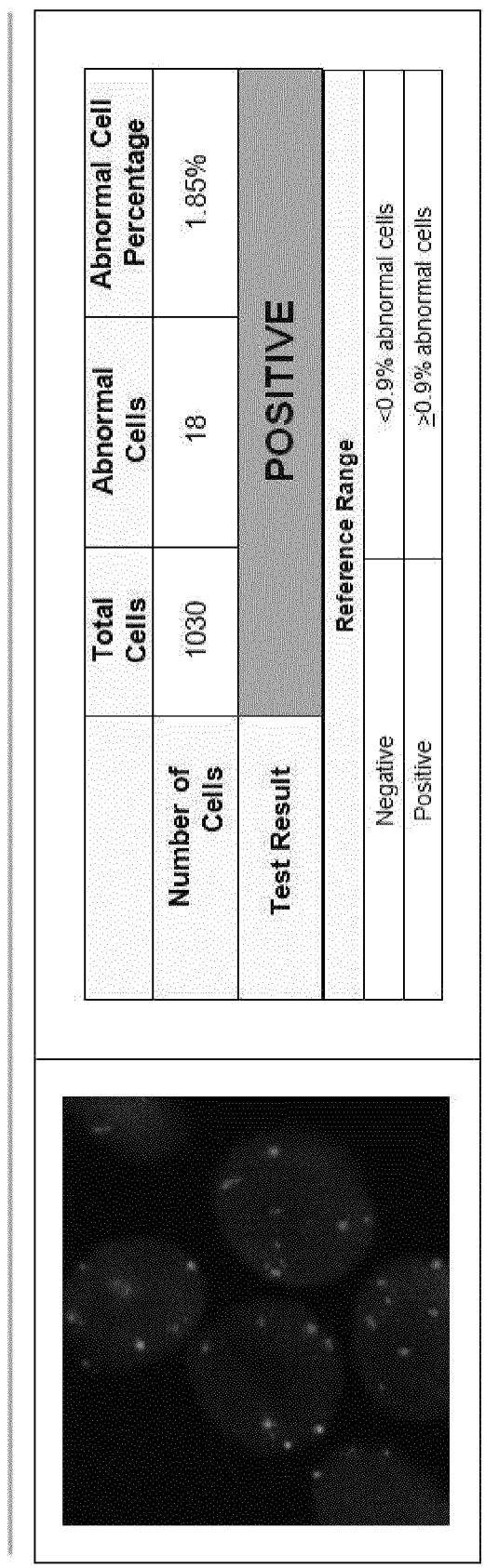
FIG. 5 is an illustration of positive results from a liquid-based cytology patient sample testing for abnormalities in 3q alone. Interpretation: Evaluation of this specimen has revealed an abnormal copy number of the TERC gene. Detailed results of the analysis are summarized in the table, along with a representative image of cells with an abnormal copy number of TERC. Materials and Methods: Analysis for the Human Telomerase gene (TERC) was performed using FISH with a probe specific for the TERC gene on chromosome region 3q26. In addition, a probe specific for chromosome 7 centromere was applied to assess DNA ploidy. Cervical cells were fixed to a slide and hybridized with these fluorescent probes. Analysis of the hybridization was performed to assess the presence of normal and abnormal cells.

Evaluation of FIG. 5 this specimen has revealed an abnormal copy number of the TERC gene. Along with a representative image of cells with an abnormal copy number of TERC. Of 1030 cells analyzed, 1012 cells were normal while 18 were found abnormal for an abnormal cell percentage of 1.85%.

Example 6

Figure 4:
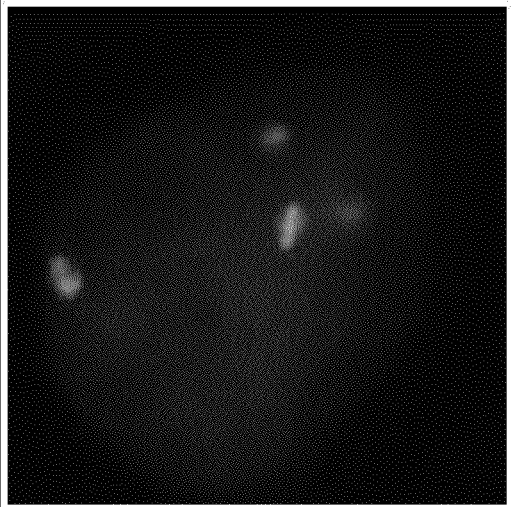
FIG. 4 is an illustration of negative results from a liquid-based cytology patient sample testing for abnormality in 3q alone. Interpretation: Evaluation of this specimen has revealed a normal copy number of the TERC gene. No Amplification of the gene at 3q26 was detected and evaluation of the chromosome 7 centromere indicates a normal diploid cell. This does not rule out other abnormalities occurring, along with a representative image of cells with a normal copy of TERC. Materials and Methods: Analysis for the Human Telomerase gene (TERC) was performed using FISH with a probe specific for the TERC gene on chromosome region 3q26. In addition, a probe specific for chromosome 7 centromere was applied to assess DNA ploidy. Cervical cells were fixed to a slide and hybridized with these fluorescent probes. Analysis of the hybridization was performed to assess the presence of normal and abnormal cells.

Evaluation of FIG. 4 revealed a normal copy number of the TERC gene. No amplification of the gene at 3q26 was detected and evaluation of the chromosome 7 centromere indicates a normal diploid cell. This does not rule out other abnormalities occurring at sites other than those listed above. Along with a representative image of cells with a normal copy of TERC. Of 800 cells analyzed, 799 cells were normal while 1 was found abnormal for an abnormal cell percentage of 0.1%.

Example 7

Tissue Fish

Figure 8:
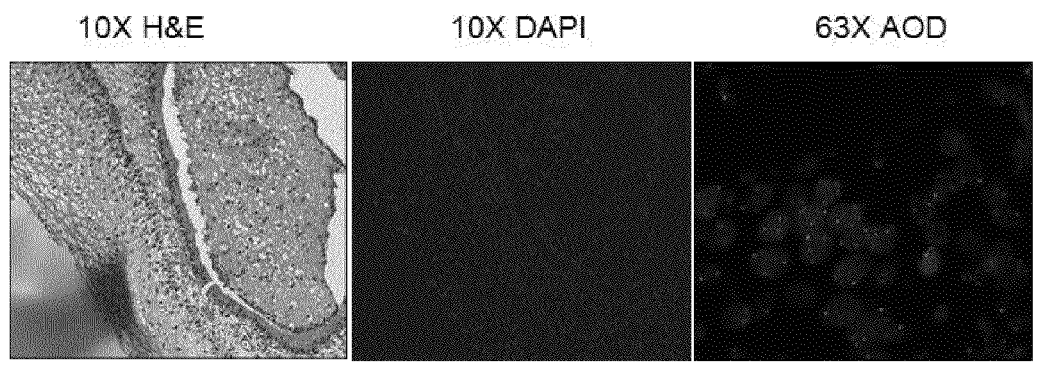
FIGS. 8 A and B is an illustration of negative results from a patient's tissue biopsy sample testing for abnormalities in 3q alone.
Figure 8:
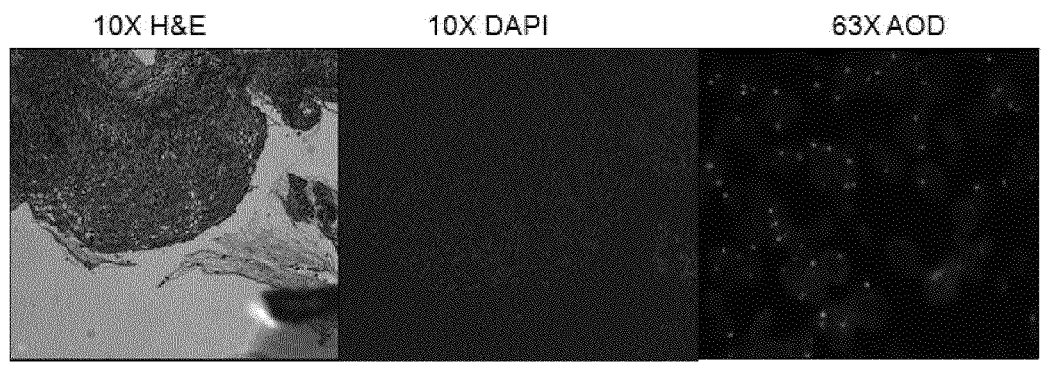
Figure 9:
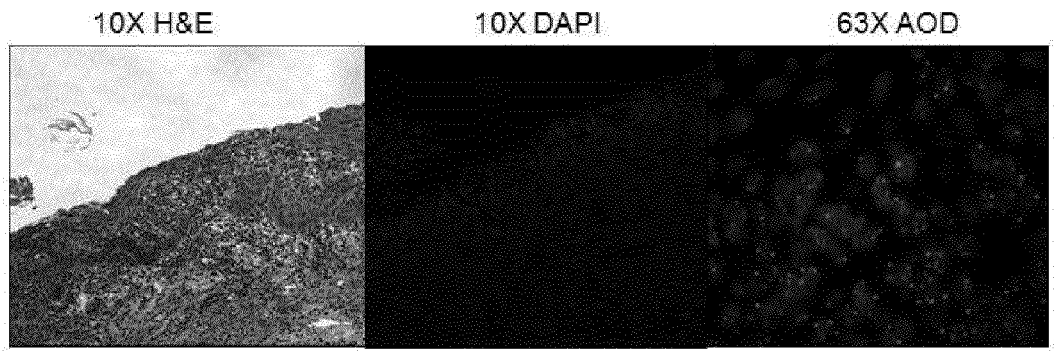
FIGS. 9 A, B, and C is an illustration of positive results from a patient's tissue biopsy sample testing for abnormalities in 3q alone.
Figure 9:
Figure 9:
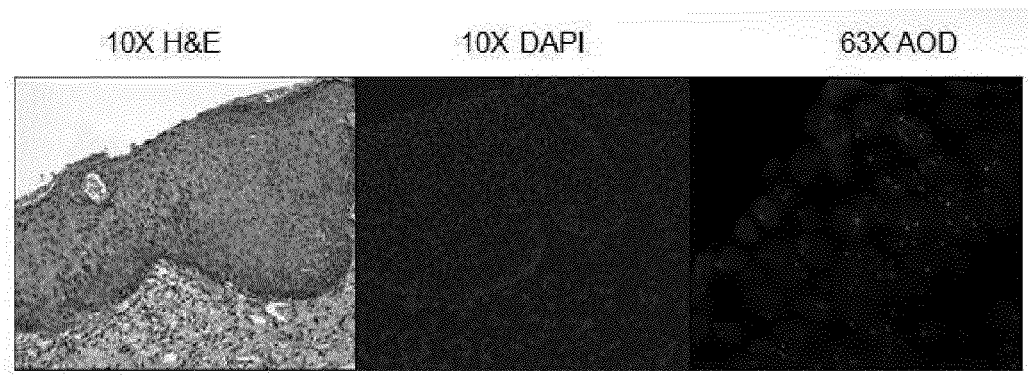

FISH was performed on 4-micron thick tissue sections cut from formalin fixed paraffin-embedded (FFPE) tissue specimens. (FIGS. 8 and 9) Slides were subject to a pretreatment protocol that includes protease digestion, washing, and dehydration. Hybridization was performed using a two-color FISH probe set containing directly labeled probes to CEN7-aqua and to the locus of 3q26 (3q-orange) (Probes obtained from Abbott Molecular). The sections were counterstained with DAPI and the cells were analyzed using fluorescence microscopy.

A minimum of fifty cells per sample were analyzed for ploidy status. Samples were judged aneuploid if the ratio of 3q26 probe signal to nuclei within the selected cells was 2.0 or greater. Samples were judged to have normal ploidy if the ratio of 3q26 probe signals to nuclei within the selected cells was less than 2. Patients with ploidy abnormalities and/or increased 3q copy number were determined at risk for a poor prognosis and are at high risk to develop more advanced cervical disease.

Results can be a diagnostic and prognostic marker for cervical dysplasia. Samples with ploidy abnormalities and/or increased 3q copy number were determined at risk for poor prognosis and to develop more advanced cervical disease.

Example 8

Figure 10:
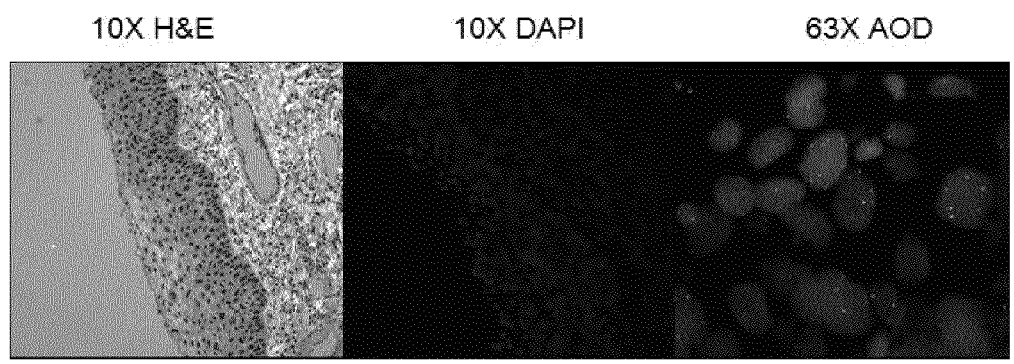
FIG. 10 is an illustration of results from a patient's tissue biopsy sample testing for abnormalities in 3q and 5p.
Figure 11:
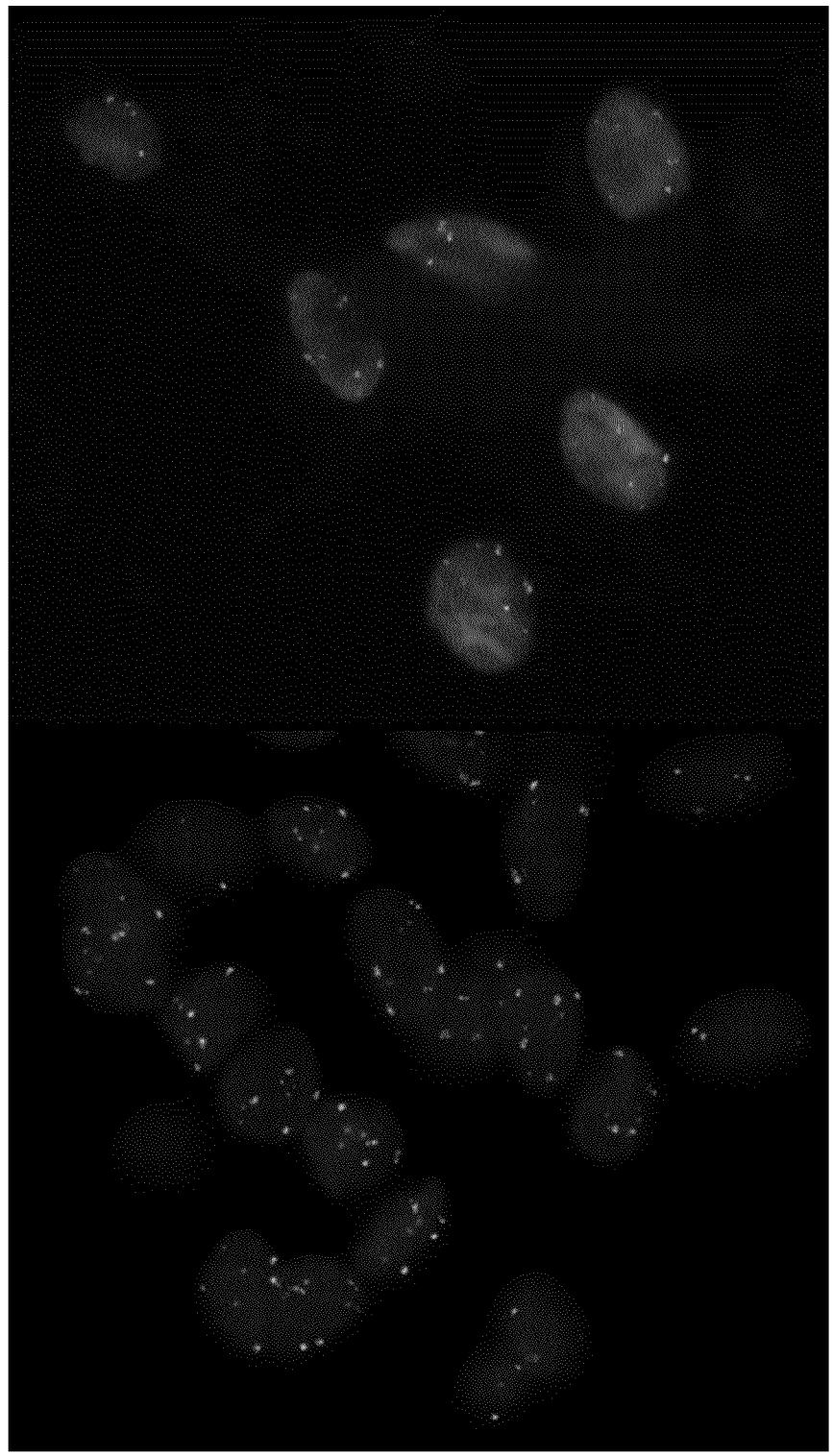
FIG. 11 is an illustration of a liquid-based cytology patient sample testing for abnormalities in 3q alone with tetraploid cells.
Figure 12:
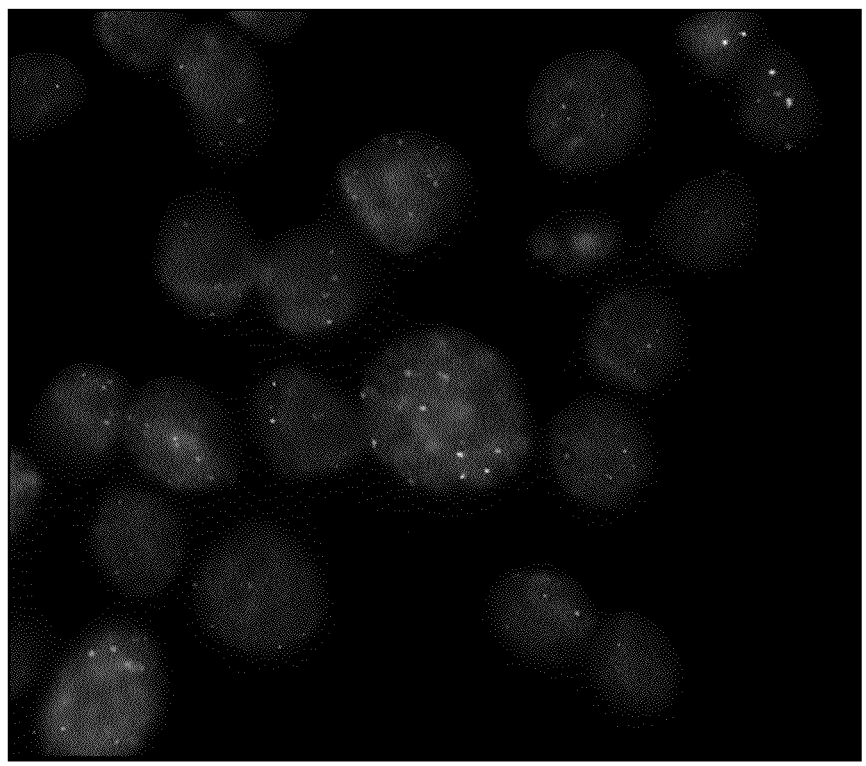
FIG. 12 is an illustration of a liquid-based cytology patient sample testing for abnormalities in 3q and 5p tetraploid cells.
Figure 13:
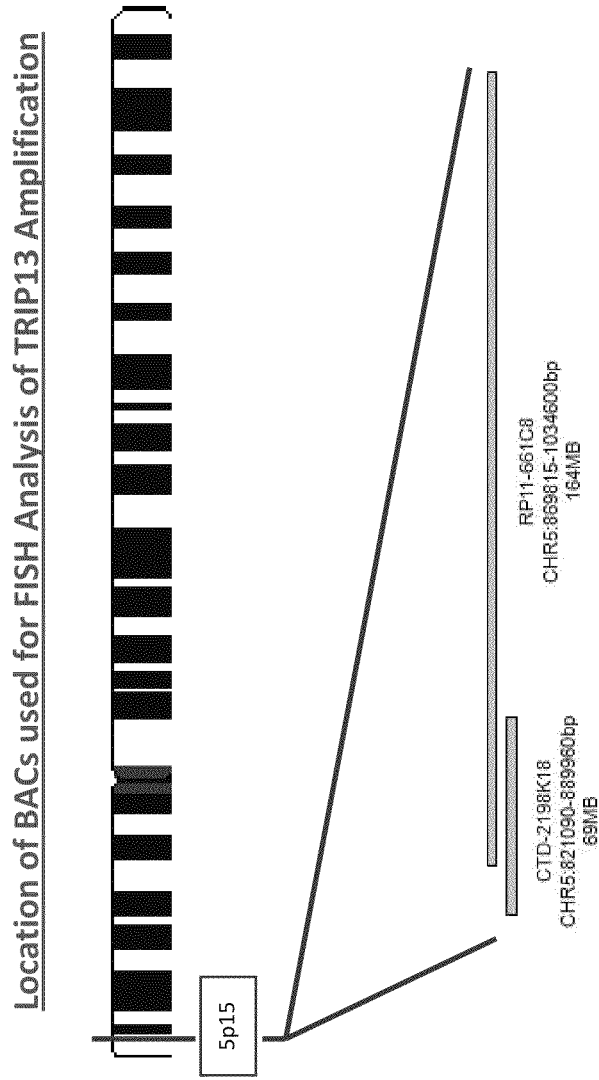
FIG. 13 illustrates clone order used to identify probes in band 5p15.33 and specific and BAC clones suitable for the production of labeled DNA probes to TRIP 13.

FISH was performed on 4-micron thick tissue sections cut from formalin fixed paraffin-embedded (FFPE) tissue specimens. (FIG. 10) Slides were subject to a pretreatment protocol that includes protease digestion, washing, and dehydration. Hybridization was performed using a three-color FISH probe set. The set included directly labeled probes to CEN7-aqua and to the locus of 3q26 (3q-orange) and to the locus of 5p15 (5p-green) (probes obtained from Abbott Molecular). The sections were counterstained with DAPI and the cells were analyzed using fluorescence microscopy. A minimum of fifty cells per sample were analyzed for ploidy status.

Samples were judged to have aneuploidy if (1) the ratio of 3q26 probe signal to nuclei within the selected cells was 2.0 or greater; (2) the ratio of 5p15 probe signal to nuclei within the selected cells was 2.0 or greater; (3) the ratio of 3q26 and 5p15 probe signals to nuclei within the selected cells was 2.0 or greater. Samples were judged to have normal ploidy if the ratio of 3q26 or 5p15 or both 3q26 & 5p15 probe signals to nuclei within the selected cells was less than 2. Samples with ploidy abnormalities and/or increased 3q copy number were determined at risk for poor prognosis and at risk to develop more advanced cervical disease.

Results can be a diagnostic and prognostic marker for cervical dysplasia. Samples with ploidy abnormalities and/or increased 3q or 5p copy number were determined at risk for a poor prognosis and at risk to develop more advanced cervical disease.

Example 9

Preparation of Working Reagents

To prepare 1% Formaldehyde Solution, add together: 2.7 mL 37% formaldehyde solution, 97.3 mL 1×PBS, 100 mL final volume. Mix thoroughly. Pour the solution into a Coplin jar. To prepare 2×SSC, add together: 100 ml 20×SSC, 900 ml dH2, 1000 ml final volume

Example 10

Ethanol Washing Solutions

Prepare dilutions of 70%, 90% using 100% ethanol and dH20. Dilutions may be used for one week unless evaporation occurs or the solution becomes diluted due to excessive use. Store at room temperature in capped containers when not in use.

To prepare 0.4×SSC/O.3% NP-40, add together: 20 ml 2×SSC, 77.7 ml dH2O, 0.3 ml NP-40, 100 ml final volume. Mix thoroughly. Discard used solution at the end of each day. To prepare 2×SSC/0.1% NP-40, add together: 99.9 ml 2×SSC, 0.1 ml NP-40, 100 ml Final Volume. Mix thoroughly. To prepare 2×SSC, 900 ml dH2O, 100 ml 20×SSC, 1000 ml final volume 1×PBS 900 ml dH2O, 100 ml 10×PBS, 1000 ml final volume 0.1M HCl 1 ml 1N HCl, 9 ml dH2O, 100 ml final volume PEPSIN (Stock Solution) (100 MG/ML) pepsin 5 g, sterile water 50 ml. Mix well. Keep on ice, make 50 μl aliquots, store at −20° C. PEPSIN (Working Solution, Prepare Fresh) 95.5 ml dH2O, 0.5 ml 1M HCl. Prewarm at 37 C (approx. 15 min.). Add 20 microliter of stock pepsin solution in clean coplan jar and add prewarmed 0.1M HCl.

Example 11

DNA Hybridization Procedure

DAY ONE PROCEDURE 1. Prepared slides on THINPREP machine (Refer to THINPREP 2000 SOP); 2. Prepared and prewarm all reagents necessary; 3. Placed slides in 2×SSC for 5 minutes at room temperature; 4. Placed slides in Protease solution for 10 minutes at 37° C. (Digestion step); 5. Placed slides in Phosphate Buffered Saline (PBS) 5 minutes at RT (Wash); 6. Placed slides in 1% Formaldehyde for 5 minutes at RT (Fixative); 7. Placed slides in 1× Phosphate Buffered Saline (PBS) 5 minutes at RT (Wash); 8. Placed slides in 70% EtOH for 1 minute at RT; 9. Placed slides in 90% EtOH for 1 minute at RT; 10. Placed slides in 100% EtOH for 1 minute at RT; 11. Dried slides; 12. Vortexed and centrifuged DNA probe and aliquot appropriate volume; 13. Added 10 ul of probe to each target area; 14. Covered with 22 mm square glass coverslip and seal with rubber cement; 15. Denatured at 72 C for 2 min.; 16. Placed slides in humidified chamber and incubate at 37° C. for 14-16 hours (overnight).

DAY TWO PROCEDURE. Prepared and prewarmed wash solutions: 1. Removed slides from humidified chamber; 2. Gently removed rubber cement and immersed slides in 2×SSC at RT to remove coverslip; 3. Placed slides in 0.4× SSC/0.3% NP-40 for 1 minute at 65° C.; 4. Removed and placed the slides in 2×SSC/0.1% NP-40 at RT for 1 minute; 5. Removed and placed slides in a dark drawer vertically to dry; 6. Applied one drop of DAPI/antifade solution onto the target area and place a coverslip (22×50 mm) over DAPI solution, avoiding air bubbles; 7. Stored slides in the dark prior to signal enumeration.

Example 12

Analysis

DNA probe set and DAPI counterstain should be viewed on an epifluorescence microscope equipped with a 100-watt mercury lamp equipped with the following filters: DAPI, Spectrum Aqua (chromosome 7 centromere), Spectrum Orange (locus on 3q26), Spectrum Green (locus on 5p15). Use the DAPI filter and a magnification of 100× and quickly scanned sample area of patient slide to determine cell quantity and quality. Began analysis in the upper left quadrant of the target area. Scanned fields with 63× oil objective from left to right and top to bottom, without re-scanning the same areas. Count a total of 1000 cells (with 1 or 2 readers). This step can be automated for high-throughput analysis. Began scanning, using Spectrum Orange filter. Counted cells with 2 normal signals for the 3q26 probe and documented. Within each field of view scanned for 3q26, switched to Spectrum Green filter and rescanned the field for 5p15 probe signals. When encountering cell with more than 2 3q26 or 5p15 signals, flipped to aqua channel and counted signals for CEN7. Any cell with more than 2 3q26 or 5p15 signals is abnormal. Filled in cell counts in appropriate column on score sheet. Cells with 4 3q26 or 5p15, and 4 CEN7 signals were tetraploid and were documented appropriately. When performing this analysis method with a two-color probe panel, the scanning, imaging, and signal documentation is modified to the reflect the actual two-color probe panel. Evaluation of specimen in FIG. 7 revealed a normal copy number of chromosomal regions 3q26 and 5p15. In the number of cells analyzed, amplification of loci at 3q26 and 5p15 was note detected and evaluation of the chromosome 7 centromere indicates a normal diploid specimen.

Example 13

Methods and Specimen Selection for Automated Analysis and Scoring

A total of twenty (20) specimens were identified within the NeoDiagnostix tested population that had negative results for cytology, HPV and two-color method testing. In addition, these 20 specimens all had 1000 total cells counted in order to minimize variation within the analysis. The triple negative specimens were considered disease negative and, therefore, any abnormal cells identified by FISH would be considered 'false positives.' Once the number of 'false positive' cells is determined for the 20 specimens, the described BETAINV calculation can be used to determine the threshold between normal and abnormal specimens.

Results: The results of FISH testing for the 20 triple negative specimens were reviewed to identify the total number of 'false positive' cells per specimen at each chromosomal loci. A specimen had 5 cells identified by FISH to be abnormal across both loci, 3q26 and 5p15, the greatest number of observed 'false positive' cells per specimen. This observation was used within the BETAINV calculation to determine the threshold between normal and abnormal specimens 95% confidence. The total number of cells entered into the equation was 1000. The BETAINV calculation returned a threshold value of 0.0104 (1.0%) or 10 cells out of 1000 counted cells. The threshold was also determined with 99% confidence and was equal to 0.0129 (1.3%) or 13 cells out of 1000.

In addition, the results of FISH testing for the 20 triple negative specimens were reviewed to identify the total number of 'false positive' cells per specimen at ONLY chromosomal locus 5p15. The specimen had 3 cells identified by FISH to be abnormal 5p15, the greatest number of observed 'false positive' cells per specimen. This observation was used within the BETAINV calculation to determine the threshold between normal and abnormal specimens 95% confidence. The total number of cells entered into the equation was 1000 from ND10107B. The BETAINV calculation returned a threshold value of 0.0077 (0.7%) or 7 cells out of 1000 counted cells. The threshold was also determined with 99% confidence and was equal to 0.0099 (0.9%) or 9 cells out of 1000.

Using the ACMG guidelines, the threshold between normal and abnormal specimens was determined for the Cervical DNA Dtex diagnostic assay. With 95% confidence, the threshold was determined to be 10 cells out of 1000 cells or 1.0% abnormal cells per specimen. Therefore, any specimen with 1.0% or greater percentage of abnormal cells by FISH is abnormal and identifies a patient with a higher risk of progression. In these cases, a POSITIVE diagnostic test result will be issued. When a specimen is found to have less than 1.0% abnormal cells per specimen, a NEGATIVE diagnostic test report will be issued.

Example 14

Cervical FISH on Biopsy Specimens: Reagents that can be used are Sodium Thiocyanate (Kreatech LK-064A); Xylene (Mallinckrodt 8668-04, 500 ml); Proteinase, bacterial Type XXIV (Sigma P8038, 100 ml). Preparation of Working Reagents: Pretreatment Solution (1M sodium thiocyanate): Freshly made for each use: 2 g sodium thiocyanate; 50 ml deionized water; and warmed to 80 C. Proteinase K: 25 mg/ml Stock solution is used by suspending 0.025 g Proteinase K in 1 ml water, store at −20 C up to one week. Freshly made for each use: 500 ul Proteinase K stock solution; 49.5 ml 2×SSC; warmed to 45 C: 2×SSC; 100 ml 20×SSC; 900 ml dH20; 1000 ml final volume. Ethanol Washing Solutions: Dilutions of 70%, 90% using 100% ethanol and dH20. Dilutions may be used for one week unless evaporation occurs or the solution becomes diluted due to excessive use and stored at room temperature in capped containers when not in use. Probe Mix: 1×TERC in Spectrum Gold; 1× Cri du Chat in Spectrum Green; 0.1×CEP 7 in Spectrum Aqua; 2×SSC/0.1% Tween-20 (pre-warm at 65 C). To prepare, add together: 20 ml 2×SSC; 77.7 ml dH2O; 0.3 ml NP-40; 100 ml final volume. Mix thoroughly.

Day One Procedure: (1) Bake 60 minutes at 65 C. (2) Deparaffinize sections 2×10 min. in xylene. (3) Dehydrate in 2×5 min. in 100% EtOH. (4) Air dry. (5) Incubate slides in pre-warmed Pretreatment Solution for 8 minutes at 80 C. (6) Wash 3 minutes at room temperature in de-ionized water. (7) Dehydrate slides in 70%, 90%, 100% EtOH, 1 min. each. (8) Air dry. (9) Incubate slides in 2×SSC for 5 min. (10) Incubate slides in pre-warmed Proteinase K solution for 10 minutes at 45 C. [Alternative to Steps 5 to 10: Incubate slides in pre-warmed Proteinase K solution for 55 minutes at 45 C. Proceed to Step 11 and continue.] (11) Rinse slides in 2×SSC for 5 min. (12) Dehydrate slides in 70%, 90%, 100% EtOH, 1 min. each. (13) Air dry. (14) Place probe mix (briefly spin down), coverslip and seal with rubber cement. Use as small a cover glass as practical for the tissue section with proportionally sized coverslips. Note: tissue sections easily trap air bubbles; this can be minimized by pipetting the probe mixture directly onto the section on the slide. (15) Co-denature at 72 C for 5 min. (16) Incubate at 37 C in a humidified chamber overnight.

Day Two Procedure: (1) Pre-warm wash 2×SSC/0.1% Tween-20 at 65 C. (2) Soak slides in 2×SSC to float off cover-slip, avoid pulling off the cover-slip to minimize shearing. (3) Wash the slides two times in 2×SSC/0.1% Tween-20 at 65 C for 5 minutes each. (4) Rinse slides for 1 minute at room temperature in 2×SSC/0.1% NP-40. (5) Remove and place slides in a dark drawer vertically to dry. (6) Coverslip with anti-fade w/DAPI (24×50 mm), store slides at 4 C.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

Fitzpatrick, M A et al., Gynecology Oncol 2006, 103:458-462
Hopman, A H N et al., J Pathol 2006, 210:412-419
Heselmeyer-Haddad, K et al., Am J Pathol 2005, 166:1229-1238
Huang, F Y et al., Cancer Genet Cytogenet 2005, 157:42-48
Heselmeyer-Haddad, K et al., Am J Pathol 2003, 163:1406-1416
Rao, P H et al., BMC Cancer 2004, 4:5-13
Heselmeyer et al., Genes, Chromosomes, & Cancer, 1997, 19:233-240
Heselmeyer et al., PNAS, 1996, 93:479-484
Andersson et al., British Journal of Cancer, 2006, 1-8
Atkin, N. B., 1997 Elsevier; 95: 33-39
Arias-Pulido, H. et. al. 2002 Mol. Cancer; 1:3
Huang F. Y. et al. 2005 Cancer Gen. and Cyto., 157: 46-47
Macville M. et al. 1999 Cancer Res.; 59:141-50
Heselmeyer K. et al. 1997 Genes Chromosomes Cancer; 19: 233-40
Rao P. H., et al. 2004 BMC Cancer; 4:5
Lockwood W. et al. Int. J. Cancer 2006; 120: 436-443.
Takuma, Y. et al. 2004 Journal of Gastroenterology and Hepatology; 19: 1300-1304
Takahashi S. et al. 2000 Eur. Jour. Of Cancer, 36: 496-502
Toshikuni, N. et al. 2000 Br. J. Cancer; 82; 833-837
Zhang A. et al. 2000 Cancer Res.; 60: 6230-6235
Zhang A. et al. 2002 Genes Chromosomes Cancer; 34: 269-75

Huang, K. F. et al., J. Formos Med. Assoc. 2007 November; 106(11):894-902
Hopman, A. H. et al., J. Pathol. 2006 December; 210(4):412-9
Jee, K. J. et al., Mod Pathol. 2001 May; 14(5):377-81
Caraway, N. P. et al., Gynecol. Oncol. 2008 July; 110(1):37-42. Epub 2008 April. 22
Heselmeyer-Haddad, K. et al., American Journal of Pathology, 2005; 166:1229-1238
Cao, Y. et al., Cancer Sci 2008 June; 99(6):1092-1099
Wolf, D. J. et al. (2007) Period Guidelines for Fluorescence In Situ Hybridization Testing.

What is claimed is:

1. A method for detecting chromosomal abnormalities in a plurality of cervical cells, said method consisting of:
   hybridizing a first nucleic acid probe to a target nucleic acid sequence on chromosome 3q of the cervical cells to form a first hybridization complex;
   hybridizing a second nucleic acid probe to a target nucleic acid on chromosome 5p of the cervical cells to form a second hybridization complex;
   hybridizing a nucleic acid control probe to centromere of chromosome 7 (CEN7) to form a third hybridization complex;
   detecting a first signal indicative of the formation of the first hybridization complex on chromosome 3q;
   detecting a second signal indicative of the formation of the second hybridization complex on chromosome 5p;
   detecting a third signal indicative of the formation of the third hybridization complex on CEN7,
   wherein said first, second and third signals indicative of formation of first, second and third hybridization complexes is indicative of an increase in chromosomal copy number in the cervical cells, and wherein the increase in chromosomal copy number is indicative of the chromosomal abnormalities in the cervical cells.

2. The method of claim 1, wherein the probes bind to target nucleic acid sequences on 5p15 and 3q26.

3. The method of claim 1, wherein the target nucleic acid sequence on 5p comprises a target at locus 5p15.33.

4. The method of claim 1, wherein the target nucleic acid sequence on 3q comprises a target at locus 3q26.1.

5. The method of claim 1, wherein the target nucleic acid sequence on chromosome arm 5p comprises a nucleic acid sequence from the TERT gene.

6. The method of claim 1, wherein the target nucleic acid sequence on chromosome arm 3q comprises nucleic acid sequences from TERC.

7. The method of claim 1, wherein the target nucleic acid sequence on chromosome arm 5p comprises nucleic acid sequences from TRIP13.

8. The method according to claim 1, wherein the target nucleic acid sequence is Cri du Chat locus 5p15.2.

9. The method according to claim 1, wherein the method further consists of a probe that binds to an additional target sequence on 1q.

10. The method according to claim 1, wherein the method further consists of a probe that binds to an additional target sequence on 1q21-31.

11. The method of claim 1, wherein tetraploidy is observed.

12. The method of claim 1, further comprising detection using FISH, CISH, PCR, ELISA, CGH, Array CGH or flow cytometry.

13. The method of claim 1, wherein the sample comprises cells sampled from the uterus, cervix, vagina, vaginal cuff, vulva, ovary or fallopian tube.

14. The method of claim 1, wherein the sample comprises metaphase cells or interphase cells.

15. The method of claim 1, wherein the cervical cells are obtained using a sampling method selected from a group consisting of pap smear, thin layer cytology specimen, thin layer suspension, fine needle aspiration, tissue specimen, punch biopsy, loop electrosurgical excision procedure (LEEP), cone biopsy, hysterectomy, and endocervical curettage (ECC).

16. The method according to claim 1, wherein the sample is derived from a patient positive for human papilloma virus infection.

17. The method of claim 1, wherein the target nucleic acid sequence on 5p comprises a target at locus 5p15.32.

18. The method of claim 1, wherein the target nucleic acid sequence on 5p comprises a target at locus 5p15.31.

19. The method of claim 1, wherein the target nucleic acid sequence on 5p comprises a target at locus 5p15.2.

20. The method of claim 1, wherein the target nucleic acid sequence on 5p comprises a target at locus 5p15.1.

21. The method of claim 1, wherein the target nucleic acid sequence on 3q comprises a target at locus 3q26.2.

22. The method of claim 1, wherein the target nucleic acid sequence on 3q comprises a target at locus 3q26.31.

23. The method of claim 1, wherein the target nucleic acid sequence on 3q comprises a target at locus 3q26.32.

24. The method of claim 1, wherein the target nucleic acid sequence on 3q comprises a target at locus 3q26.33.

25. The method according to claim 1, wherein the method further consists of a probe that binds to an additional target sequence on 20q.

26. The method according to claim 1, wherein the method further consists of a probe that binds to an additional target sequence on 12q.

27. The method according to claim 1, wherein the method further consists of a probe that binds to an additional target sequence 19q.

28. The method according to claim 1, wherein the method further consists of a probe that binds to an additional target sequence on 11q.

29. The method according to claim 1, wherein the method further consists of a probe that binds to an additional target sequence on 6q.

30. The method according to claim 1, wherein the method further consists of a probe that binds to an additional target sequence on 17p.

31. The method according to claim 1, wherein the method further consists of a probe that binds to an additional target sequence on 7.

32. The method according to claim 1, wherein the method further consists of a probe that binds to an additional target sequence on 8q.

33. The method according to claim 1, wherein the method further consists of a probe that binds to an additional target sequence on 9q.

34. The method according to claim 1, wherein the method further consists of a probe that binds to an additional target sequence on 16q.

35. The method according to claim 1, wherein the method further consists of a probe that binds to an additional target sequence on 2q.

36. The method according to claim 1, wherein the method further consists of a probe that binds to an additional target sequence on 9p.

37. The method according to claim 1, wherein the method further consists of a probe that binds to an additional target sequence on 10q.

38. The method according to claim 1, wherein the method further consists of a probe that binds to an additional target sequence on 18p.

39. The method according to claim 1, wherein the method further consists of a probe that binds to an additional target sequence on 20q12.

40. The method according to claim 1, wherein the method further consists of a probe that binds to an additional target sequence on 12q13-24.

41. The method according to claim 1, wherein the method further consists of a probe that binds to an additional target sequence on 19q13.

42. The method according to claim 1, wherein the method further consists of a probe that binds to an additional target sequence on 11q21.

43. The method according to claim 1, wherein the method further consists of a probe that binds to an additional target sequence on 7q11-22.

44. The method according to claim 1, wherein the method further consists of a probe that binds to an additional target sequence on 8q24.

45. The method according to claim 1, wherein the method further consists of a probe that binds to an additional target sequence on 9q33-34.

46. The method according to claim 1, wherein the method further consists of a probe that binds to an additional target sequence on 16q23.

47. The method according to claim 1, wherein the method further consists of a probe that binds to an additional target sequence on 2q32.

48. The method according to claim 1, wherein the method further consists of a probe that binds to an additional target sequence on 9p22.

49. The method according to claim 1, wherein the method further consists of a probe that binds to an additional target sequence on 10q21-24.

50. The method according to claim 1, wherein the method further consists of a probe that binds to an additional target sequence on 18p11.

51. A method for detecting chromosomal abnormalities in a plurality of cervical cells, said method comprising:
  hybridizing a first nucleic acid probe to a target nucleic acid sequence on chromosome 3q of the cervical cells to form a first hybridization complex;
  hybridizing a second nucleic acid probe to a target nucleic acid on chromosome 5p of the cervical cells to form a second hybridization complex;
  hybridizing a nucleic acid control probe to centromere of chromosome 7 (CEN7) to form a third hybridization complex;
  detecting a first signal indicative of the formation of the first hybridization complex on chromosome 3q;
  detecting a second signal indicative of the formation of the second hybridization complex on chromosome 5p;
  detecting a third signal indicative of the formation of the third hybridization complex on CEN7,
  wherein said first, second and third signals indicative of formation of first, second and third hybridization complexes is indicative of an increase in chromosomal copy number in the cervical cells, and wherein a lack of chromosomal abnormalities in the cervical cells is shown by normal ploidy and
  (1) less than 1.0% of analyzed cells with an increase in both 3q copy number and 5p copy number;
  (2) gains of only 3q copy number in less than 0.9% of the analyzed cells; or
  (3) gains of only 5p copy number in less than 0.7% of the analyzed cells.

52. The method of claim 51, wherein the probes bind to target nucleic acid sequences on 5p15 and 3q26.

53. The method of claim 51, wherein the target nucleic acid sequence on 5p comprises a target at locus 5p15.33.

54. The method of claim 51, wherein the target nucleic acid sequence on 5p comprises a target at locus 5p15.32.

55. The method of claim 51, wherein the target nucleic acid sequence on 5p comprises a target at locus 5p15.31.

56. The method of claim 51, wherein the target nucleic acid sequence on 5p comprises a target at locus 5p15.2.

57. The method of claim 51, wherein the target nucleic acid sequence on 5p comprises a target at locus 5p15.1.

58. The method of claim 51, wherein the target nucleic acid sequence on 3q comprises a target at locus 3q26.1.

59. The method of claim 51, wherein the target nucleic acid sequence on 3q comprises a target at locus 3q26.2.

60. The method of claim 51, wherein the target nucleic acid sequence on 3q comprises a target at locus 3q26.31.

61. The method of claim 51, wherein the target nucleic acid sequence on 3q comprises a target at locus 3q26.32.

62. The method of claim 51, wherein the target nucleic acid sequence on 3q comprises a target at locus 3q26.33.

63. The method of claim 51, wherein the target nucleic acid sequence on chromosome arm 5p comprises a nucleic acid sequence from the TERT gene.

64. The method of claim 51, wherein the target nucleic acid sequence on chromosome arm 3q comprises a nucleic acid sequence from TERC.

65. The method of claim 51, wherein the target nucleic acid sequence on chromosome arm 5p comprises a nucleic acid sequence from TRIP13.

66. The method according to claim 51, wherein the target nucleic acid sequence is Cri du Chat locus 5p15.2.

67. The method according to claim 51, wherein the method further comprises a probe that binds to an additional target sequence on 1q.

68. The method according to claim 51, wherein the method further comprises a probe that binds to an additional target sequence on 20q.

69. The method according to claim 51, wherein the method further comprises a probe that binds to an additional target sequence on 12q.

70. The method according to claim 51, wherein the method further comprises a probe that binds to an additional target sequence 19q.

71. The method according to claim 51, wherein the method further comprises a probe that binds to an additional target sequence on 11q.

72. The method according to claim 51, wherein the method further comprises a probe that binds to an additional target sequence on 6q.

73. The method according to claim 51, wherein the method further comprises a probe that binds to an additional target sequence on 17p.

74. The method according to claim 51, wherein the method further comprises a probe that binds to an additional target sequence on 7.

75. The method according to claim 51, wherein the method further comprises a probe that binds to an additional target sequence on 8q.

76. The method according to claim 51, wherein the method further comprises a probe that binds to an additional target sequence on 9q.

77. The method according to claim 51, wherein the method further comprises a probe that binds to an additional target sequence on 16q.

78. The method according to claim 51, wherein the method further comprises a probe that binds to an additional target sequence on 2q.

79. The method according to claim 51, wherein the method further comprises a probe that binds to an additional target sequence on 9p.

80. The method according to claim 51, wherein the method further comprises a probe that binds to an additional target sequence on 10q.

81. The method according to claim 51, wherein the method further comprises a probe that binds to an additional target sequence on 18p.

82. The method according to claim 51, wherein the method further comprises a probe that binds to an additional target sequence on 1q21-31.

83. The method according to claim 51, wherein the method further comprises a probe that binds to an additional target sequence on 20q12.

84. The method according to claim 51, wherein the method further comprises a probe that binds to an additional target sequence on 12q13-24.

85. The method according to claim 51, wherein the method further comprises a probe that binds to an additional target sequence on 19q13.

86. The method according to claim 51, wherein the method further comprises a probe that binds to an additional target sequence on 11q21.

87. The method according to claim 51, wherein the method further comprises a probe that binds to an additional target sequence on 7q11-22.

88. The method according to claim 51, wherein the method further comprises a probe that binds to an additional target sequence on 8q24.

89. The method according to claim 51, wherein the method further comprises a probe that binds to an additional target sequence on 9q33-34.

90. The method according to claim 51, wherein the method further comprises a probe that binds to an additional target sequence on 16q23.

91. The method according to claim 51, wherein the method further comprises a probe that binds to an additional target sequence on 2q32.

92. The method according to claim 51, wherein the method further comprises a probe that binds to an additional target sequence on 9p22.

93. The method according to claim 51, wherein the method further comprises a probe that binds to an additional target sequence on 10q21-24.

94. The method according to claim 51, wherein the method further comprises a probe that binds to an additional target sequence on 18p11.

95. The method of claim 51, wherein tetraploidy is observed.

96. The method of claim 51, further comprising detection using FISH, CISH, PCR, ELISA, CGH, Array CGH or flow cytometry.

97. The method of claim 51, wherein the sample comprises cells sampled from the uterus, cervix, vagina, vaginal cuff, vulva, ovary or fallopian tube.

98. The method of claim 51, wherein the sample comprises metaphase cells or interphase cells.

99. The method of claim 51, wherein the cervical cells are obtained using a sampling method selected from a group consisting of pap smear, thin layer cytology specimen, thin layer suspension, fine needle aspiration, tissue specimen, punch biopsy, loop electrosurgical excision procedure (LEEP), cone biopsy, hysterectomy, and endocervical curettage (ECC).

100. The method according to claim 51, wherein the sample is derived from a patient positive for human papilloma virus infection.

* * * * *